(12) United States Patent
Auvin et al.

(10) Patent No.: US 7,465,721 B2
(45) Date of Patent: Dec. 16, 2008

(54) 2-HYDROXYTETRAHYDROFURAN DERIVATIVES AND USE THEREOF AS MEDICAMENTS

(75) Inventors: Serge Auvin, Palaiseau (FR); Pierre-Etienne Chabrier de Lassauniere, Paris (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 0 days.

(21) Appl. No.: 10/532,731

(22) PCT Filed: Dec. 8, 2004

(86) PCT No.: PCT/FR2004/003147

§ 371 (c)(1),
(2), (4) Date: Apr. 26, 2005

(87) PCT Pub. No.: WO2005/056551

PCT Pub. Date: Jun. 23, 2005

(65) Prior Publication Data

US 2006/0166893 A1   Jul. 27, 2006

(30) Foreign Application Priority Data

Dec. 9, 2003   (FR) .................................. 03 14368

(51) Int. Cl.
*C07D 417/02* (2006.01)
*A61K 31/5415* (2006.01)

(52) U.S. Cl. ................... 514/214.01; 540/588; 514/249; 514/411; 514/225.2; 514/229.8; 544/35; 544/38; 544/41; 544/102; 544/347

(58) Field of Classification Search ................ 514/249, 514/411, 214.01, 225.2, 229.8; 540/588; 544/35, 38, 41, 102, 347; 548/440
See application file for complete search history.

(56) References Cited

OTHER PUBLICATIONS

Wang et al. PubMed Abstract 1994, Trends Pharmacol Sci. 15(11):412-9, Nov. 1994. (one page abstract).*
Damasio, Alzheimer's Disease and Related Dementias, Cecil Textbook of Medicine, 20th Edition, vol. 2, pp. 1992-1996, 1996.*
Douglas, Jr. Introduction to Viral Diseases, Cecil Textbook of Medicine, 20th Edition, vol. 2, pp. 1739-1747, 1996.*
Simone, Oncology: Introduction, Cecil Textbook of Medicine, 20th Edition, vol. 1, pp. 1004-1010, 1996.*
Carragher, PubMed Abstract (Curr Pharm Des. 12(5):615-38), 2006 (one page abstract).*
Layzer, Degenerative Diseases of the Nervous System, Cecil Textbook of Medicine, 20th Edition, vol. 2, pp. 2050-2057, 1996.*

* cited by examiner

*Primary Examiner*—Kahsay T Habte
(74) *Attorney, Agent, or Firm*—Charles A. Muserlian

(57) ABSTRACT

A hydroxytetrahydrofuran of formula

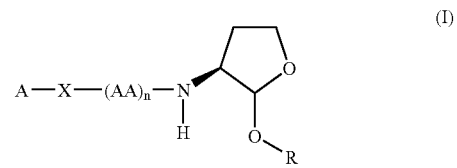

(I)

wherein A is

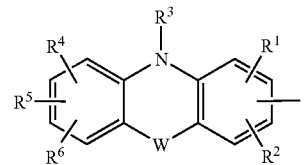

with the substituents as defined in the specification, having a calpain inhibiting activity and/or an activity which traps the reactive oxygen species useful for treating inflammatory and immunological diseases, cardio-vascular and cerebro-vascular diseases, disorders of the central or peripheral nervous system, osteoporosis, muscular dystrophy, proliferative diseases, cataract, rejection reactions following organ transplants and autoimmune and viral diseases.

4 Claims, No Drawings

2-HYDROXYTETRAHYDROFURAN DERIVATIVES AND USE THEREOF AS MEDICAMENTS

This application is a 371 of PCT/FR2004/003147 filed Dec. 8, 2004.

The present invention relates to novel derivatives of 2-hydroxytetrahydrofuran having a calpain inhibiting activity and/or an activity which traps the reactive oxygen species (ROS). The invention also relates to their preparation methods, the pharmaceutical preparations containing them and their use for therapeutic purposes, in particular as calpain inhibitors and traps for reactive oxygen species in a selective or non-selective manner.

Given the potential role of calpains and ROS's in physiopathology, the novel derivatives according to the invention can produce beneficial or favourable effects in the treatment of pathologies where these enzymes and/or these radical species are involved, and in particular:

- inflammatory and immunological diseases such as for example rheumatoid arthritis, pancreatitis, multiple sclerosis, inflammations of the gastro-intestinal system (ulcerative or non-ulcerative colitis, Crohn's disease),
- cardiovascular and cerebrovascular diseases including for example arterial hypertension, septic shock, cardiac or cerebral infarctions of ischaemic or haemorrhagic origin, ischaemias as well as disorders linked to platelet aggregation,
- disorders of the central or peripheral nervous system such as for example neurodegenerative diseases where there can in particular be mentioned cerebral or spinal cord trauma, sub-arachnoid haemorrhage, epilepsy, ageing, senile dementia including Alzheimer's disease, Huntington's chorea, Parkinson's disease, peripheral neuropathies,
- loss of hearing,
- osteoporosis,
- muscular dystrophies,
- proliferative diseases such as for example atherosclerosis or recurrence of stenosis,
- cataract,
- organ transplants,
- auto-immune and viral diseases such as for example lupus, AIDS, parasitic and viral infections, diabetes and its complications, multiple sclerosis,
- cancer,
- all pathologies characterized by an excessive production of ROS's and/or calpain activation.

In all these pathologies, there is experimental evidence demonstrating the involvement of ROS's (Free Radic. Biol. Med. (1996) 20, 675-705; Antioxid. Health. Dis. (1997) 4 (Handbook of Synthetic Antioxidants), 1-52) as well as the involvement of calpains (Trends Pharmacol. Sci. (1994) 15, 412419; Drug News Perspect (1999) 12, 73-82). As an example, cerebral lesions associated with cerebral infarctions or with experimental cranial traumatism are reduced by antioxodant agents (Acta. Physiol. Scand. (1994) 152, 349-350; J. Cereb. Blood Flow Metabol. (1995) 15, 948-952; J Pharmacol Exp Ther (1997) 2, 895-904) as well as by calpain inhibitors (Proc Natl Acad Sci USA (1996) 93, 3428-33; Stroke, (1998) 29, 152-158; Stroke (1994) 25, 2265-2270).

The Applicant had already described in the patent application PCT WO 01/32654 heterocyclic compounds having at the same time a calpain inhibiting activity and an activity which traps reactive forms of oxygen.

Said heterocyclic compounds of said patent application correspond to general formula (A1)

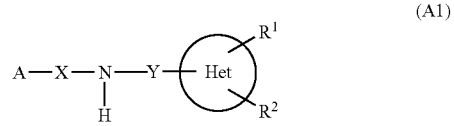

(A1)

in which
  $R^1$ represents a hydrogen atom, an —$OR^3$, —$SR^3$, oxo or a cyclic acetal radical,
    in which $R^3$ represents a hydrogen atom, an alkyl, aralkyl, heterocycloalkylcarbonyl, alkylcarbonyl, arylcarbonyl or aralkylcarbonyl radical,
    in which the alkyl, aryl or heterocycloalkyl radical are optionally substituted by one or more identical or different substituents chosen from: alkyl, OH, alkoxy, nitro, cyano, halogen or —$NR^4R^5$;
  $R^4$ and $R^5$ represent, independently, a hydrogen atom or an alkyl radical, or $R^4$ and $R^5$ form together with the nitrogen atom to which they are attached an optionally substituted heterocycle,
  $R^2$ represents a hydrogen atom, an alkyl, aryl or aralkyl radical, the aryl group being optionally substituted by one or more identical or different radicals chosen from: —$OR^6$, —$NR^7R^8$, halogen, cyano, nitro or alkyl,
    in which $R^6$, $R^7$ and $R^8$ represent, independently, a hydrogen atom, an alkyl, aryl, aralkyl, alkylcarbonyl, arylcarbonyl or aralkylcarbonyl radical;
  A represents in particular an optionally substituted phenothiazinyl radical;
  X represents —$(CH_2)_n$—, —$(CH_2)_n$—CO—, —N($R^{45}$)—CO—$(CH_2)_n$—CO—, —N($R^{45}$)—CO—D—CO—, —CO—N($R^{45}$)—D—CO—, —CO—D—CO—, —CH=CH—$(CH_2)_n$—CO—, —N($R^{45}$)—$(CH_2)_n$—CO—, —N($R^{45}$)—CO—C($R^{46}R^{47}$)—CO—, —O—$(CH_2)_n$—CO—, —N($R^{45}$)—CO—NH—C($R^{46}R^{47}$)—CO—, —CO—N($R^{45}$)—C($R^{46}R^{47}$)—CO—, —S—$(CH_2)_n$—CO— or —Z—CO—;
  D represents an optionally substituted phenylene radical;
  Z represents a heterocycle,
  $R^{45}$ represents a hydrogen atom or an alkyl radical,
  $R^{46}$ and $R^{47}$ represent, independently, a hydrogen atom, an alkyl, aryl or aralkyl radical the alkyl and aryl groups of which are optionally substituted;
  $R^{48}$ and $R^{49}$ represent, independently, a hydrogen atom, an alkyl radical or a —$COR^{50}$ group, or $R^{48}$ and $R^{49}$ form together with the nitrogen atom to which they are attached an optionally substituted heterocycle,
  $R^{50}$ represents a hydrogen atom, an alkyl, alkoxy or —$NR^{51}R^{52}$ radical,
  $R^{51}$ and $R^{52}$ represent, independently, a hydrogen atom or an alkyl radical, or $R^{51}$ and $R^{52}$ form together with the nitrogen atom to which they are attached, an optionally substituted heterocycle;
  n being an integer comprised between 0 and 6;
  Y represents —$(CH_2)_p$—, —C($R^{53}R^{54}$)—$(CH_2)_p$—, —C($R^{53}R^{54}$)—CO—;
  $R^{53}$ and $R^{54}$ represent, independently, a hydrogen atom, an alkyl radical, an aralkyl radical the aryl group of which is optionally substituted by one or more identical or different substituents chosen from: the OH, halogen, nitro, alkyl, alkoxy, —$NR^{55}R^{56}$ group,
  $R^{55}$ and $R^{56}$ represent, independently, a hydrogen atom, an alkyl radical or a —$COR^{57}$ group, or $R^{55}$ and $R^{56}$ form together with the nitrogen atom to which they are attached, an optionally substituted heterocycle, $R^{57}$ represents a hydrogen atom, an alkyl, alkoxy or —$NR^{58}R^{59}$ radical, $R^{58}$ and $R^{59}$ represent, independently, a hydrogen atom or an alkyl radical, or $R^{58}$ and $R^{59}$ form together with the nitrogen atom to which they are attached an optionally substituted heterocycle;

p being an integer comprised between 0 and 6;

Het represents a heterocycle, as well as the addition salts with mineral and organic acids or with mineral and organic bases of said compounds of general formula (A1), with the exception of the compounds of formula (A1) in which when Het represents tetrahydrofuran or tetrahydropyran, $R^1$ the $OR^3$ radical with $R^3$ representing a hydrogen atom, an alkyl, arylalkyl, heterocycloalkylcarbonyl radical the heterocycloalkyl radical of which is branched by a carbon atom, alkylcarbonyl, arylcarbonyl or aralkylcarbonyl, $R^2$ a hydrogen and Y the —$(CH_2)_p$— radical with p=0, then X does not represent —CO—$N(R^{45})$—$C(R^{46}R^{47})$—CO— with $R^{45}$=$R^{46}$=H.

The Applicant has now surprisingly found that the compounds of general formula (I) described hereafter have at the same time a calpain inhibiting activity and an activity which traps the reactive oxygen species whilst possessing improved properties in terms of cell penetration.

A subject of the present invention is therefore the compounds of general formula (I)

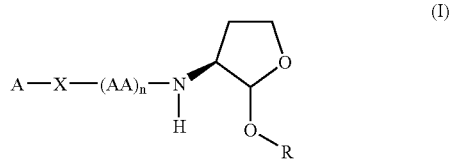

(I)

in which:

A represents the

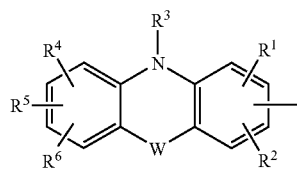

radical in which $R^1$, $R^2$, $R^4$, $R^5$ and $R^6$ represent, independently, a hydrogen atom, a halogen atom, the OH group, an alkyl, alkoxy, cyano, nitro or $NR^7R^8$ radical, $R^7$ and $R^8$ represent, independently, a hydrogen atom, an alkyl radical or a —$COR^9$ group, $R^9$ represents a hydrogen atom, an alkyl or alkoxy radical, $R^3$ represents a hydrogen atom, an alkyl radical or a —$COR^{10}$ group, $R^{10}$ represents a hydrogen atom or an alkyl or alkoxy radical, and W represents a bond or a —$CH_2CH_2$—, —CH=CH—, —O—, —S— or —$NR^{11}$— radical in which $R^{11}$ represents a hydrogen atom or an alkyl radical;

X represents —CO—, —Y—CO—, —O—Y—CO— or —$NR^{12}$—Y—CO—,

Y represents an alkylene or haloalkylene radical, $R^{12}$ represents a hydrogen atom, an alkyl radical or a —$COR^{13}$ group, $R^{13}$ represents a hydrogen atom, an alkyl, haloalkyl or alkoxy radical, AA represents, each time that it occurs, a natural amino acid, a natural amino acid the side chain of which carries a reactive chemical function (such as carboxylic acid, amine, alcohol or thiol) is protected in the form of alkyl or aralkyl ester (for the acid functions), alkyl or aralkyl carbamate or alkyl or aralkyl carboxamide (for the amine functions), in the form of alkyl or aralkyl ether or alkyl or aralkyl thioether or in the form of alkyl or aralkyl ester (for the alcohol and thiol functions) or finally an amino acid of general formula —$NR^{14}$—$(CH_2)_p$—$CR^{15}R^{16}$—CO— in which p represents 0 or 1, $R^{14}$ represetns a hydrogen atom or an alkyl radical, $R^{15}$ represents a hydrogen atom or an alkyl radical and $R^{16}$ a hydrogen atom, an alkyl, haloalkyl, phenyl, cycloalkyl, cycloalkylalkyl or alkenyl radical, or $R^{15}$ and $R^{16}$ forming with the carbon atom to which they are attached a saturated carbocycle with 3 to 7 carbon atoms (and preferably with 3 to 6 carbon atoms), an —$(AA)_2$— group also being able to represent a carbapeptide of general formula —$NR^{17}$—$(CH_2)_3$—$CH(R^{18})$—CO— in which $R^{17}$ represents a hydrogen atom or an alkyl radical and $R^{18}$ represents a hydrogen atom or an alkyl radical;

n represents 2 or 3; and finally

R represents a hydrogen atom or an alkyl or —CO—$R^{19}$ radical in which $R^{19}$ represents an alkyl radical (and in particular methyl);

or the salts of such compounds.

By alkyl or alkylene, unless otherwise specified, is meant a linear or branched alkyl or alkylene radical containing 1 to 12 carbon atoms, and preferably 1 to 6 carbon atoms. By haloalkyl or haloalkylene is meant an alkyl or alkylene radical at least one of the hydrogen atoms of which is substituted by a halogen atom. By alkenyl, unless otherwise specified, is meant a linear or branched alkenyl radical containing 2 to 12 carbon atoms, and preferably 2 to 6 carbon atoms. By cycloalkyl, unless otherwise specified, is meant a cycloalkyl radical containing 3 to 7 carbon atoms. By alkoxy, unless otherwise specified, is meant an alkoxy radical the carbon chain of which is linear or branched and contains 1 to 6 carbon atoms. By aryl, unless otherwise specified, is meant a carbocyclic aryl radical. By carbocyclic aryl is meant a carbocyclic aryl radical comprising 1 to 3 fused rings. Finally, by halogen atom is meant an atom chosen from the fluorine, chlorine, bromine and iodine atoms.

By the aralkyl and cycloalkylalkyl radicals is meant respectively the aralkyl and cycloalkylalkyl radicals the alkyl, aryl and cycloalkyl radicals of which, which constitute them, have the meanings previously indicated.

By natural amino acid is meant valine (Val), leucine (Leu), isoleucine (Ile), methionine (Met), phenylalanine (Phe), asparagine (Asn), glutamic acid (Glu), glutamine (Gln), histidine (His), lysine (Lys), arginine (arg), aspartic acid (Asp), glycine (Gly), alanine (Ala), serine (Ser), threonine (Thr), tyrosine (Tyr), tryptophan (Trp), cysteine (Cys) or proline (Pro).

By linear or branched alkyl having 1 to 6 carbon atoms is meant in particular the methyl, ethyl, propyl, isopropyl, butyl, isobutyl, sec-butyl and tert-butyl, pentyl, neopentyl, isopentyl, hexyl, isohexyl radicals. By cycloalkyl containing 3 to 7 carbon atoms is meant in particular a cyclohexyl radical. By carbocyclic aryl is meant in particular the phenyl, naphthyl and phenantryl radicals, preferably the phenyl and naphthyl radicals and more preferentially the phenyl radical. By haloalkyl is meant in particular the —$CF_3$ radical. Finally, by haloalkylene is meant in particular the —$CF_2$-radical.

Examples of protected functions carried by side chains of natural amino acids include in particular:
- protected acid functions in the form of methyl, ethyl, tert-butyl or benzyl ester;
- protected amine functions in the form of tert-butyl or benzyl carbamate, acetamide;
- protected alcohol functions in the form of tert-butyl, benzyl ether or pyran or also in the form of acetyl; and
- protected thiol functions in the form of methyl thioethers or in the form of methyl thioesters.

Preferably, the compounds of the invention are such that they possess at least one of the following characteristics:
- $R^1$, $R^2$, $R^4$, $R^5$ and $R^6$ represent, independently, a hydrogen atom, a halogen atom or an alkyl, alkoxy or $NR^7R^8$ radical;
- $R^3$ represents a hydrogen atom, a methyl radical or a —$COR^9$ radical in which $R^9$ represents a methyl or tert-butoxy radical;
- W represents a bond or a —$CH_2CH_2$—, —CH=CH—, —)— or —S— radical;
- X represents —CO—, —Y—CO— or —O—Y—CO;
- —$(AA)_n$— contains amino acids chosen independently from the group constituted by the natural amino acids, 3-methylvaline, norvaline, phenylglycine, vinylglycine and 2-aminobutyric acid;
- n represents 2;
- R represents a hydrogen atom or a methyl radical.

More preferentially, the compounds of the invention are such that they possess at least one of the following characteristics:
- $R^1$, $R^2$, $R^4$, $R^5$ and $R^6$ represent, independently, a hydrogen atom or an alkyl or alkoxy radical (and, still more preferentially, $R^1$, $R^2$, $R^4$, $R^5$ and $R^6$ are all hydrogen atoms);
- $R^3$ represents a hydrogen atom or a methyl radical (and, still more preferentially, a hydrogen atom);
- W represents —S—;
- X represents —Y—CO— or —O—Y—CO—;
- —$(AA)_n$— represents an —$(AA^2)$—$(AA^1)$— group such that $AA^1$ represents Leu and $AA^2$ represents an amino acid chosen from the group constituted by the natural amino acids, 3-methylvaline, norvaline, phenylglycine, vinylglycine and 2-aminobutyric acid (and, still more preferentially, an —$(AA^2)$—$(AA^1)$— group such that $AA^1$ represents Leu and $AA^2$ represents an amino acid chosen from the group constituted by Leu, Lys, Val, 3-methylvaline, norvaline, phenylglycine, vinylglycine and 2-aminobutyric acid);
- R represents a hydrogen atom.

In particular, the invention relates to a compound of general formula (I) chosen from the following compounds;

N-(10H-phenothiazin-2-ylcarbonyl)-L-leucyl-L-leucyl-$N^1$-[(3S)-2-methoxytetrahydrofuran-3-yl]-L-leucinamide;
N-(10H-phenothiazin-2-ylcarbonyl)-L-leucyl-L-leucyl-$N^1$-[(3S)-2-hydroxytetrahydrofuran-3-yl]-L-leucinamide;
N-(10H-phenothiazin-2-ylcarbonyl)glycyl-$N^1$-[(3S)-2-methoxytetrahydrofuran-3-yl]-L-leucinamide;
N-(10H-phenothiazin-2-ylcarbonyl)leucyl-$N^1$-[(3S)-2-methoxytetrahydrofuran-3-yl]-L-leucinamide;
$N^6$-[(benzyloxy)carbonyl]-$N^2$-(10H-phenothiazin-2-ylcarbonyl)lysyl-$N^1$-[(3S)-2-methoxytetrahydrofuran-3-yl]-L-leucinamide;
1-(10H-phenothiazin-2-ylcarbonyl)-L-prolyl-$N^1$-[(3S)-2-methoxytetrahydrofuran-3-yl]-L-leucinamide;
N-(10H-phenothiazin-2-ylcarbonyl)glycyl-$N^1$-[(3S)-2-hydroxytetrahydrofuran-3-yl]-L-leucinamide;
N-(10H-phenothiazin-2-ylcarbonyl)leucyl-$N^1$-[(3S)-2-hydroxytetrahydrofuran-3-yl]-L-leucinamide;
$N^6$-[(benzyloxy)carbonyl]-$N^2$-(10H-phenothiazin-2-ylcarbonyl)lysyl-$N^1$-[(3S)-2-hydroxytetrahydrofuran-3-yl]-L-leucinamide;
1-(10H-phenothiazin-2-ylcarbonyl)-L-prolyl-$N^1$-[(3S)-2-hydroxytetrahydrofuran-3-yl]-L-leucinamide;
N-(10H-phenothiazin-2-ylcarbonyl)leucyl-$N^1$-[(3S)-2-(acetyloxy)-tetrahydrofuran-3-yl]-L-leucinamide;
$N^2$-(10H-phenothiazin-2-ylcarbonyl)lysyl-$N^1$-[(3S)-2-hydroxytetrahydrofuran-3-yl]-L-leucinamide;
N-(10H-phenothiazin-2-ylacetyl)-L-leucyl-$N^1$-[(3S)-2-methoxytetrahydrofuran-3-yl]-L-leucinamide;
O-(tert-butyl)-N-(10H-phenothiazin-2-ylacetyl)-L-seryl-$N^1$-[(3S)-2-methoxytetrahydrofuran-3-yl]-L-leucinamide;
N-(10H-phenothiazin-2-ylacetyl)-L-alanyl-3-cyclohexyl-$N^1$-[(3S)-2-methoxytetrahydrofuran-3-yl]-L-alaninamide;
N-(10H-phenothiazin-2-ylacetyl)-L-leucyl-$N^1$-[(3S)-2-hydroxytetrahydrofuran-3-yl]-L-leucinamide;
O-(tert-butyl)-N-(10H-phenothiazin-2-ylacetyl)-L-seryl-$N^1$-[(3S)-2-hydroxytetrahydrofuran-3-yl]-L-leucinamide;
N-(10H-phenothiazin-2-ylacetyl)-L-alanyl-3-cyclohexyl-$N^1$-[(3S)-2-hydroxytetrahydrofuran-3-yl]-L-alaninamide;
N-[3-(10H-phenothiazin-2-yl)propanoyl]-L-leucyl-$N^1$-[(3S)-2-methoxytetrahydrofuran-3-yl]-L-leucinamide;
N-[3-(10H-phenothiazin-2-yl)propanoyl]-L-leucyl-$N^1$-[(3S)-2-hydroxytetrahydrofuran-3-yl]-L-leucinamide;
N-[(10H-phenothiazin-2-yloxy)acetyl]-L-leucyl-$N^1$-[(3S)-2-methoxytetrahydrofuran-3-yl]-L-leucinamide;
N-[(10H-phenothiazin-2-yloxy)acetyl]-glycyl-$N^1$-[(3S)-2-methoxytetrahydrofuran-3-yl]-L-leucinamide;
N-[(10H-phenothiazin-2-yloxy)acetyl]-L-alanyl-$N^1$-[(3S)-2-methoxytetrahydrofuran-3-yl]-L-leucinamide;
N-[(10H-phenothiazin-2-yloxy)acetyl]-L-valyl-$N^1$-[(3S)-2-methoxytetrahydrofuran-3-yl]-L-leucinamide;
N-[(10H-phenothiazin-2-yloxy)acetyl]-β-alanyl-$N^1$-[(3S)-2-methoxytetrahydrofuran-3-yl]-L-leucinamide;
N-methyl-N-[(10H-phenothiazin-2-yloxy)acetyl]glycyl-$N^1$-[(3S)-2-methoxytetrahydrofuran-3-yl]-L-leucinamide;
N-[(10H-phenothiazin-2-yloxy)acetyl]-D-valyl-$N^1$-[(3S)-2-methoxytetrahydrofuran-3-yl]-L-leucinamide;
3-methyl-N-[(10H-phenothiazin-2-yloxy)acetyl]-L-valyl-$N^1$-[(3S)-2-methoxytetrahydrofuran-3-yl]-L-leucinamide;
$N^1$-[(3S)-2-methoxytetrahydrofuran-3-yl]-$N^2$-((2S)-2-{[(10H-phenothiazin-2-yloxy)-acetyl]amino}butanoyl)-L-leucinamide;
N-[(10H-phenothiazin-2-yloxy)acetyl]-L-norvalyl-$N^1$-[(3S)-2-methoxytetrahydrofuran-3-yl]-L-leucinamide;
N-[(10H-phenothiazin-2-yloxy)acetyl]-L-seryl-$N^1$-[(3S)-2-methoxytetrahydrofuran-3-yl]-L-leucinamide;
N-[(10H-phenothiazin-2-yloxy)acetyl]-L-threonyl-$N^1$-[(3S)-2-methoxytetrahydrofuran-3-yl]-L-leucinamide;
$N^1$-[(3S)-2-methoxytetrahydrofuran-3-yl]-$N^2$-((2S)-2-{[(10H-phenothiazin-2-yloxy)acetyl]amino}-2-phenylethanoyl)-L-leucinamide;
$N^1$-[(3S)-2-methoxytetrahydrofuran-3-yl]-$N^2$-((2S)-2-{[(10H-phenothiazin-2-yloxy)acetyl]amino}but-3-enoyl)-L-leucinamide;
2-methyl-N-[(10H-phenothiazin-2-yloxy)acetyl]alanyl-$N^1$-[(3S)-2-methoxytetrahydrofuran-3-yl]-L-leucinamide;
N-[(10H-phenothiazin-2-yloxy)acetyl]-glycyl-$N^1$-[(3S)-2-methoxytetrahydrofuran-3-yl]-L-valinamide;

N-[(10H-phenothiazin-2-yloxy)acetyl]-glycyl-3-cyclo-hexyl-N$^1$-[(3S)-2-methoxytetrahydrofuran-3-yl]-L-alaninamide;

N-[(10H-phenothiazin-2-yloxy)acethy]-glycyl-N-[(3S)-2-methoxytetrahydrofuran-3-yl]-L-phenylalaninamide;

N-[(10H-phenothiazin-2-yloxy)acetyl]glycyl-N$^2$-isobutyl-N$^1$-[(3S)-2-methoxytetrahydrofuran-3-yl]glycinamide;

N-[(10H-phenothiazin-2-yloxy)acetyl]-L-leucyl-N$^1$-[(3S)-2-hydroxytetrahydrofuran-3-yl]-L-leucinamide;

N-[(10H-phenothiazin-2-yloxy)acetyl]-glycyl-N$^1$-[(3S)-2-hydroxytetrahydrofuran-3-yl]-L-leucinamide;

N-[(10H-phenothiazin-2-yloxy)acetyl]-L-alanyl-N$^1$-[(3S)-2-hydroxytetrahydrofuran-3-yl]-L-leucinamide;

N-[(10H-phenothiazin-2-yloxy)acetyl]-L-valyl-N$^1$-[(3S)-2-hydroxytetrahydrofuran-3-yl]-L-leucinamide;

N-[(10H-phenothiazin-2-yloxy)acetyl]-β-alanyl-N$^1$-[(3S)-2-hydroxytetrahydrofuran-3-yl]-L-leucinamide;

N-methyl-N-[(10H-phenothiazin-2-yloxy)acetyl]glycyl-N$^1$-[(3S)-2-hydroxytetrahydrofuran-3-yl]-L-leucinamide;

N-[(10H-phenothiazin-2-yloxy)acetyl]-D-valyl-N$^1$-[(3S)-2-hydroxytetrahydrofuran-3-yl]-L-leucinamide;

3-methyl-N-[(10H-phenothiazin-2-yloxy)acetyl]-L-valyl-N$^1$-[(3S)-2-hydroxytetrahydrofuran-3-yl]-L-leucinamide;

N$^1$-[(3S)-2-hydroxytetrahydrofuran-3-yl]-N$^2$-((2S)-2-{[(10H-phenothiazin-2-yloxy)acetyl]amino}butanoyl)-L-leucinamide;

N-[(10H-phenothiazin-2-yloxy)acetyl]-L-norvalyl-N$^1$-[(3S)-2-hydroxytetrahydrofuran-3-yl]-L-leucinamide;

N-[(10H-phenothiazin-2-yloxy)acetyl]-L-seryl-N$^1$-[(3S)-2-hydroxytetrahydrofuran-3-yl]-L-leucinamide;

N-[(10H-phenothiazin-2-yloxy)acetyl]-L-threonyl-N$^1$-[(3S)-2-hydroxytetrahydrofuran-3-yl]-L-leucinamide;

N$^1$-[(3S)-2-hydroxytetrahydrofuran-3-yl]-N$^2$-((2S)-2-{[(10H-phenothiazin-2-yloxy)acetyl]amino}-2-phenylethanoyl)-L-leucinamide;

N$^1$-[(3S)-2-hydroxytetrahydrofuran-3-yl]-N$^2$-((2S)-2-{[(10H-phenothiazin-2-yloxy)-acetyl]amino}but-3-enoyl)-L-leucinamide;

2-methyl-N-[(10H-phenothiazin-2-yloxy)acetyl]alanyl-N$^1$-[(3S)-2-hydroxytetrahydrofuran-3-yl]-L-leucinamide;

N-[(10H-phenothiazin-2-yloxy)acetyl]glycyl-N$^1$-[(3S)-2-hydroxytetrahydrofuran-3-yl]-L-valinamide;

N-[(10H-phenothiazin-2-yloxy)acetyl]glycyl-3-cyclohexyl-N$^1$-[(3S)-2-hydroxytetrahydrofuran-3-yl]-L-alaninamide;

N-[(10H-phenothiazin-2-yloxy)acetyl]glycyl-N-[(3S)-2-hydroxytetrahydrofuran-3-yl]-L-phenylalaninamide;

N-[(10H-phenothiazin-2-yloxy)acetyl]glycyl-N$^1$-[(3S)-2-hydroxytetrahydrofuran-3-yl]-N$^2$-isobutylglycinamide;

N-[2-methyl-2-(10H-phenothiazin-2-yloxy)propanoyl]glycyl-N$^1$-[(3S)-2-methoxytetrahydrofuran-3-yl]-L-leucinamide;

N-[2-methyl-2-(10H-phenothiazin-2-yloxy)propanoyl]glycyl-N$^1$-[(3S)-2-hydroxytetrahydrofuran-3-yl]-L-leucinamide;

N-(10,11-dihydro-5H-dibenzo[b,f]azepin-3-ylcarbonyl)-L-leucyl-N$^1$-[(3S)-2-methoxytetrahydrofuran-3-yl]-L-leucinamide;

N-(10,11-dihydro-5H-dibenzo[b,f]azepin-3-ylcarbonyl)-L-leucyl-N$^1$-[(3S)-2-hydroxytetrahydrofuran-3-yl]-L-leucinamide;

N-[(5-acetyl-10,11-dihydro-5H-dibenzo[b,f]azepin-3-yl)carbonyl]-L-leucyl-N$^1$-[(3S)-2-methoxytetrahydrofuran-3-yl]-L-leucinamide;

2-methyl-N-[(10H-phenothiazin-2-yloxy)acetyl]alanyl-N$^1$-[(3S)-2-hydroxytetrahydrofuran-3-yl]-L-leucinamide;

or a salt of one of the latter.

A subject of the present invention is also, as medicaments, the compounds of general formula (I) as defined previously, as well as the pharmaceutically acceptable salts of such compounds.

By pharmaceutically acceptable salt is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", Int. J. Pharm. (1986), 33, 201-217.

The invention also relates to the pharmaceutical compositions containing, as active ingredient, a compound of general formula (I) as defined previously, or a pharmaceutically acceptable salt of such a compound, with at least one pharmaceutically acceptable excipient.

The pharmaceutical compositions containing a compound of the invention can be in the form of a solid, for example powders, granules, tablets, gelatin capsules, liposomes, suppositories or patches. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water.

The invention moreover relates to the use of a compound of general formula (I) as defined previously, or of a pharmaceutically acceptable salt of such a compound, for preparing a medicament intended to treat all the pathologies characterized by an excessive ROS production and/or a calpain activation, and in particular the diseases and disorders chosen from the group constituted by the inflammatory and immunological diseases, cardio-vascular and cerebro-vascular diseases, disorders of the central or peripheral nervous system, osteoporosis, muscular dystrophy, proliferative diseases, cataract, rejection reactions following organ transplants and autoimmune and viral diseases.

The administration of a medicament according to the invention can be carried out by topical route, oral route, parenteral route, by intramuscular injection, by subcutaneous injection, by intravenous injection, etc.

The dose of a product according to the present invention, to be provided for treatment of the abovementioned diseases or disorders, varies depending on the administration method, the age and bodyweight of the subject to be treated as well as the state of the latter, and will be finally decided by the attending doctor or vet. Such a quantity determined by the attending doctor or vet is here called the "therapeutically effective quantity".

By way of indication, the administration dose envisaged for a medicament according to the invention is comprised between 0.1 mg and 10 g depending on the type of active ingredient used.

According to the invention, the compounds of general formula (I) can be prepared by the processes described hereafter.

Preparation of the Compounds of General Formula (I)

The compounds of furmula (I) according to the invention can be prepared according to the synthesis route represented in Diagram 1 below (the compounds of general formula (I) in which R represents an alkyl radical Alk being called the compounds of general formula $(I)_1$, those of general formula (I) in which R represents a hydrogen atom being called the compounds of general formula $(I)_2$ and those of general formula (I) in which R represents $—COR^{19}$ being called the compounds of general formula $(I)_3$ in the remainder of the specification):

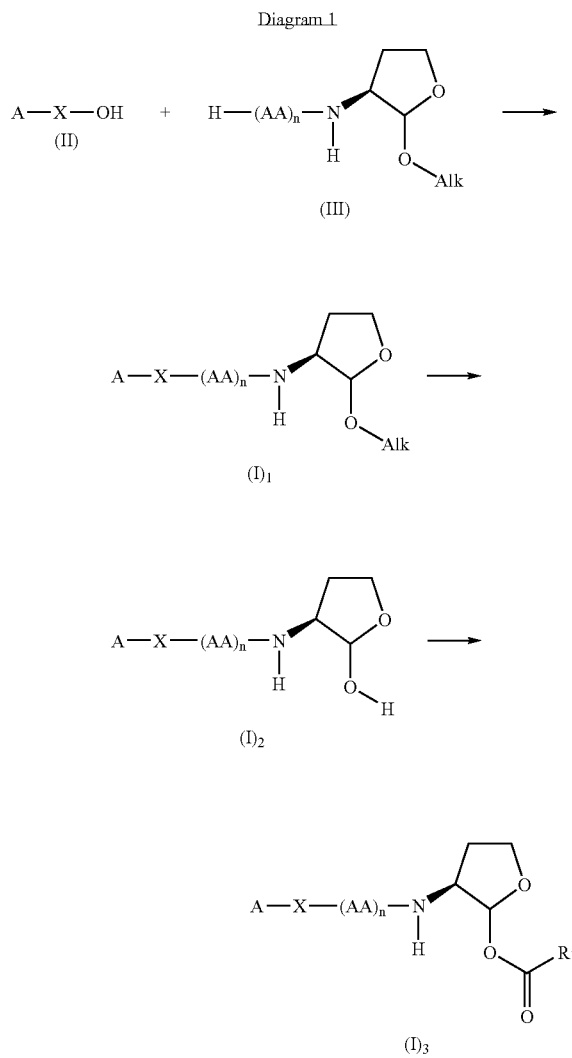

The compounds of general formulae $(I)_1$ and $(I)_2$ in which A, X, AA, n and R are as described previously are prepared, Diagram 1, by condensation of the acids of general formula (II) with the amines of general formula (III), under the standard conditions of peptide synthesis (M. Bodanszky and A. Bodanszky, The Practice of Peptide Synthesis, 145 (Springer-Verlag, 1984)) in THF, dichloromethane or DMF in the presence of a coupling reagent such as dicyclohexylcarbodiimide (DCC), 1,1'-carbonyldiimidazole (CDI) (J. Med. Chem. (1992), 35 (23), 4464-4472) or 1-(3-dimethylaminopropyl)-3-ethylcarbodiimide hydrochloride (EDC or WSCI) (John Jones, The Chemical Synthesis of Peptides, 54 (Clarendon Press, Oxford, 1991)) and of a base such as, for example, triethylamine or N,N-diisopropylethylamine, in order to lead to the compounds of general formula $(I)_1$. The hemiacetalic function of the compounds of general formula $(I)_1$ can then be deprotected using an approximately 2N aqueous solution of a mineral acid, such as for example, HCl or HBr, using acetone as co-solvent. The lactol derivatives of general formula $(I)_2$ thus obtained can if appropriate be acylated using, in particular, an acid anhydride $(R^{19}CO)_2O$ (for example acetic anhydride) in the presence of an acylation agent such as N,N-dimethyl-4-pyridinamine in order to lead to the compounds of general formula $(I)_3$.

Preparation of the Intermediates of General Formula (II)

The non-commercial carboxylic acids of general formula (II) in which A, W, X, Y, $R^1$, $R^2$, $R^3$, $R^4$, $R^5$ and $R^6$ are as described above, are accessible according to different synthesis routes described in detail hereafter.

When X=—O—Y—CO—:

In this case, a synthesis route such as that represented in Diagram 2 hereafter can be used.

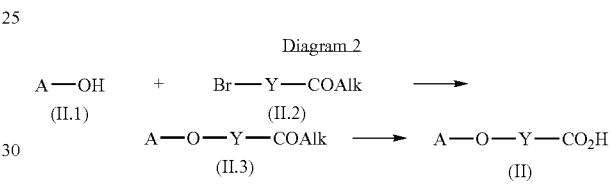

According to this synthesis route, the acids of general formula (II) in which X represents —O—Y—CO—, Diagram 2, can be prepared from, for example, hydroxy-phenothiazines (J. Med. Chem. (1992), 35(4), 716-24) or hydroxycarbazoles (J. Chem. Soc (1955), 3475-3477; J. Med. Chem. (1964), 7, 158-161) of general formula (II.1). The condensation with commercial halogenoesters of general formula (II.2) is carried out in the presence of a base such as for example $K_2CO_3$ or $Cs_2CO_3$, by heating in a polar solvent such as, for example, THF or DMF, for at least 5 hours. The esters of general formula (II.3) obtained as intermediates are then deprotected (in acid medium in the case of the tert-butyl esters or by saponification for the methyl/ethyl esters) in order to lead to the acids of general formula (II) in which X represents the —O—Y—CO— group.

When X=—CO—:

In this case, synthesis routes such as those represented in Diagrams 3 or 4 hereafter can if appropriate be used.

i) X represents —CO— and W represents —S—, —O— or a bond: derivatives of phenothiazine or carbazole of general formula (II) can be obtained from 2-acetylphenothiazines (e.g. Pharmazie (1984), 39(1), 22-3; Bull. Soc. Chim. (1968), (7), 2832-42, Pharmazie (1966), 21(11), 645-9) or 2-acetylcarbazoles (e.g. Heterocycles (1994), 39(2), 833-45; J. Indian Chem. Soc. (1985), 62(7), 534-6; J. Chem. Soc. Chem. Comm. (1985), (2), 86-7) of general formula (II.4) which are N-acetylated using acetyl chloride, by heating to reflux in toluene, in order to lead to the intermediates (II.5) (J. Med. Chem. (1998), 41(2), 148-156). The intermediates (II.5) thus obtained are successively treated by a mixture of iodine and pyridine (J. Amer. chem. Soc. (1944), 66, 894-895) and by aqueous soda, at 100° C., in order to lead to the carboxylic acids of general formula (II).

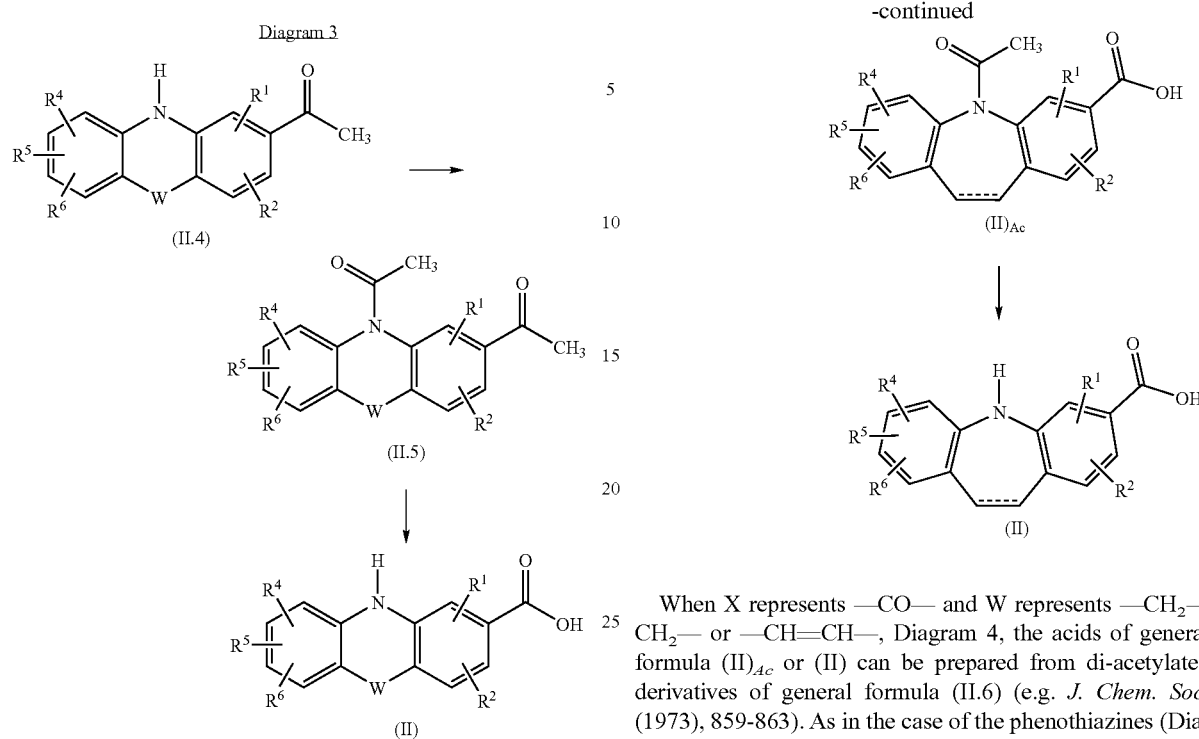

ii) X represents —CO— and W represents —CH$_2$—CH$_2$— or —CH=CH—:

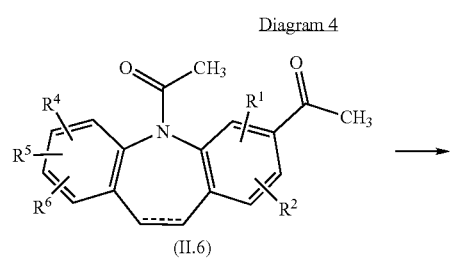

When X represents —CO— and W represents —CH$_2$—CH$_2$— or —CH=CH—, Diagram 4, the acids of general formula (II)$_{Ac}$ or (II) can be prepared from di-acetylated derivatives of general formula (II.6) (e.g. *J. Chem. Soc.* (1973), 859-863). As in the case of the phenothiazines (Diagram 3), the oxidation of the acetyl is carried out using iodine and pyridine followed by hydrolysis in aqueous soda, while warm. The compounds of general formula (II)$_{Ac}$ thus obtained (which are compounds of general formula (II) in which R$^3$ represents an acetyl group) can optionally undergo additional treatment in the presence of aqueous potash, under reflux, for a time preferably comprised between 15 and 36 hours in order to lead to the carboxylic acids of general formula (II).

When X=—Y—CO—:

For X=—Y—CO—, two synthetic routes represented in Diagram 5 hereafter make it possible to access the carboxylic acids of general formula (II), according to the availability of the starting reagents.

Diagram 5

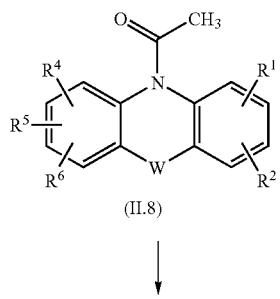

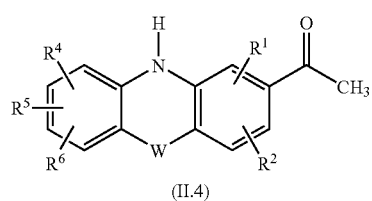

(II.4)

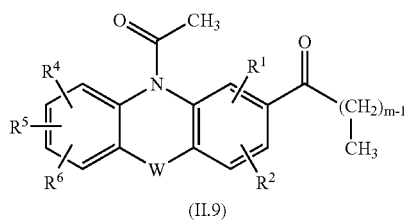

(II.9)

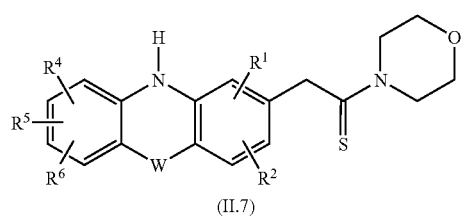

(II.7)

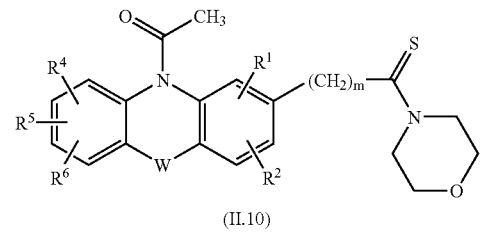

(II.10)

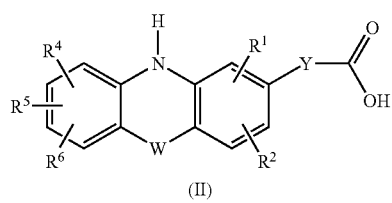

(II)

In the case of the 2-acetylphenothiazines (W=—S—) or 2-acetylcarbazoles (W represents a bond) of general formula (II.4), described previously, the conversion to carboxylic acid of general formula (II) is carried out (left-hand part of Diagram 5) by a Willgerodt-Kindler-type homologation reaction (*Synthesis* (1975), 358-375). Heating of the intermediates of general formula (II.4) in the presence of sulphur and morpholine leads to the formation of the thiocarboxamides of general formula (II.7) (German patent applications DE 2702714 and DE 1910291) which are converted by hydrolysis to carboxylic acids of general formula (II).

Alternatively (right-hand part of Diagram 5), when W represents —S— or a bond and m is an integer greater than 1, or when W represents —$CH_2$—$CH_2$— or —CH=CH— and m is an integer greater than or equal to 1, the synthesis of the carboxylic acids of general formula (II) starts with the acylation of the aromatic ring of the intermediates of general formula (II.8) by an alkanoyl chloride in $CS_2$, according to the Friedel-Crafts reaction conditions (*J. Amer. Chem. Soc.* (1946), 68, 2673-78; *J. Chem. Soc. Perkin Trans.* 1 (1973), 859-861). The acylated intermediates of general formula (II.9) are then converted to thiocarboxyamide derivatives of general formula (II.10), by the Willgerodt-Kindler reaction, and finally to carboxylic acids of general formula (II) according to the chemical sequence described previously.

Preparation of the Intermediates of General Formula (III)

The amino-lactol derivatives of general formula (III), in which AA, R and n are as described above, are accessible using the preparation route represented in Diagram 6 hereafter. This process allows preparation of the compounds of general formula (III) in which n=2 (hereafter the compounds of general formula (III)$_2$) and the compounds of general formula (III) in which n=3 (hereafter the compounds of general formula (III)$_3$).

Diagram 6

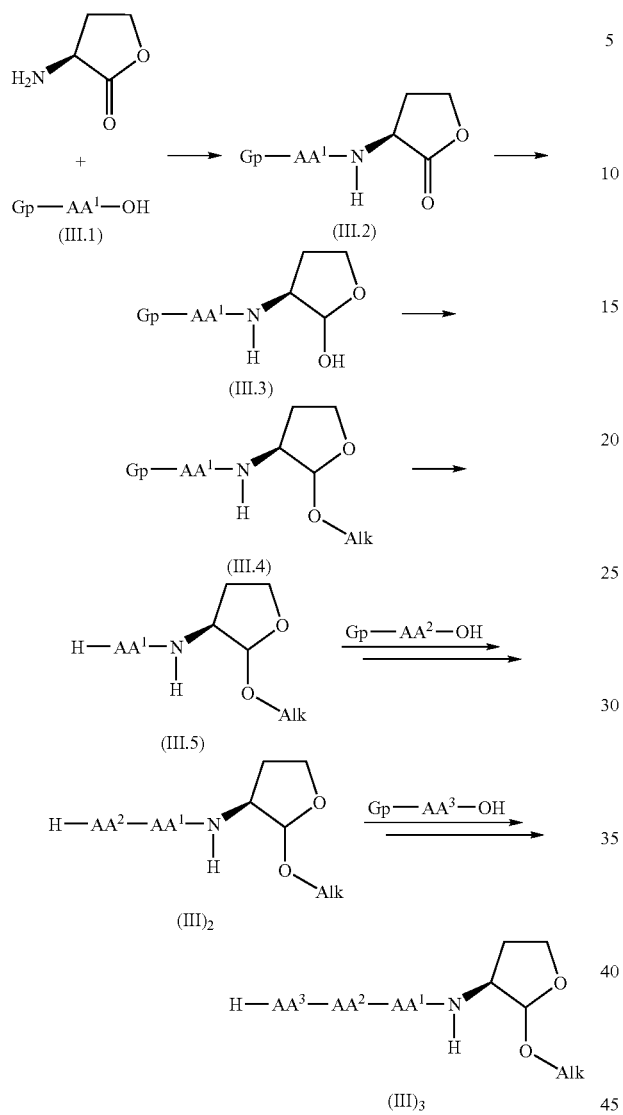

Diagram 7

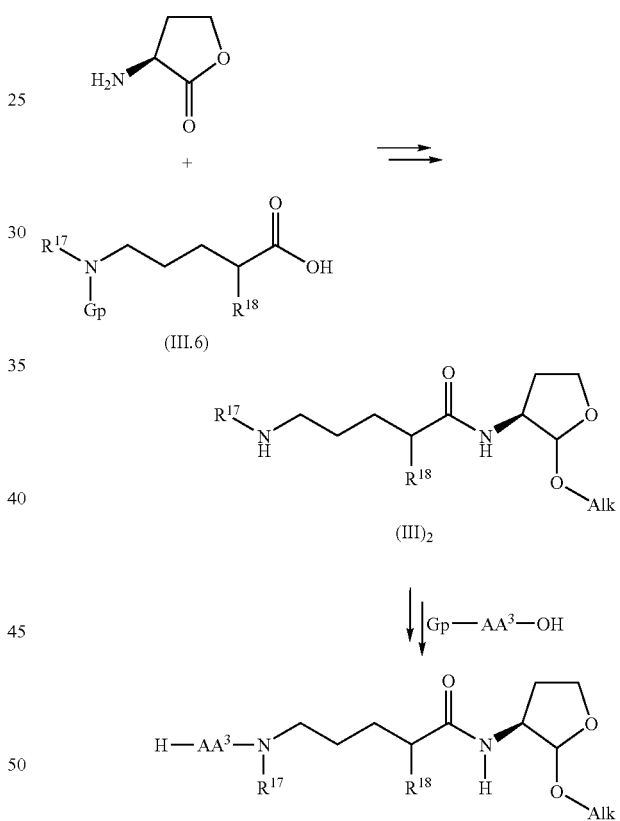

Organic Synthesis, Second edition (Wiley-Interscience, 1991)). The intermediates of general formula (III.5) are then subjected to one or two successive elongation-deprotection cycles of the peptide chain, as described previously, in order to obtain the di- (n=2) or tri-peptide (n=3) derivatives of respective general formulae (III)$_2$ and (III)$_3$.

In the particular case where the (AA$^2$—AA$^1$) group or the (AA$^3$—AA$^2$) group is replaced by a carbapeptide of general formula —NR$^{17}$—(CH$_2$)$_3$—CH(R$^{18}$)—CO—, the derivatives of general formula (III)$_2$ and (III)$_3$ can be obtained according to a peptide synthesis strategy analogous to that described previously represented in Diagram 7 hereafter (which only represents the situation where the (AA$^2$—AA$^1$) group is replaced by a carbapeptide—an analogous preparation process can be used for the case where the (AA$^3$—AA$^2$) group is replaced by a carbapeptide).

The amino-butyrolactone derivatives of general formula (III.2) are obtained by condensation of the protected amino acids of general formula (III.1), in which AA$^1$ is an amino acid radical AA as defined previously in general formula (I) and Gp is a protective group such as, for example, a benzyl or tert-butyl carbamate, with (S)-α-aminobutyrolactone under the standard conditions of peptide synthesis in order to lead to the carboxamide intermediates of general formula (III.2). The lactone is then reduced to lactol using a reducing agent such as, for example, diisobutylaluminum hydride (DIBAL), in an inert solvent such as, for example, THF or CH$_2$Cl$_2$, at a temperature preferably below −50° C., for example at approximately −78° C. The hemiacetalic function of the lactol derivatives of general formula (III.3) is then protected in alcoholic medium, for example in methanol, using a strong acid such as, for example, trifluoroacetic acid, in order to lead to the acetals of general formula (III.4). The amine function of the amino-acetal derivatives of general formula (III.4) is then deprotected according to methods described in the literature (T. W. Greene and P. G. M. Wuts, Protective Groups in The carbapeptides of general formula (III.6) are themselves accessible from processes described in the literature (e.g, *Int. J. Peptide Protein Res.* (1992), 39, 273-277).

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no case be considered as a limit to the scope of the invention.

EXAMPLES

Example 1

N-(10H-Phenothiazin-2-ylcarbonyl)-L-Leucyl-L-Leucyl-N[1]-[(3S)-2-Methoxytetrahydrofuran-3-yl]-L-Leucinamide 1.1) N[2]-[(Benzyloxy)Carbonyl]-N[1]-[(3S)-2-Oxotetrahydrofuran-3-yl]-L-Leucinamide 3.51 g (13.25 mmol) of Cbz-L-Leucine, 2.41 g (1 eq.) of (S)-2-amino-4-butyrolactone hydrobromide, 1.97 g of HOBT (1.1 eq.) and 5.59 g (2.2 eq.) of 1-(3-dimethylaminopropyl)-3-ethylcarbodiimide hydrochloride (EDC) is dissolved in 60 ml of anhydrous DMF then 7.64 ml (3.3 eq.) of N,N-diisopropylethylamine is added. The reaction mixture is stirred for 15 hours at 20° C. before being poured into 200 ml of a 1/1 mixture of ethyl acetate/water. After stirring and decantation, the organic solution is washed successively with 100 ml of a saturated solution of NaHCO$_3$, 50 ml of water, 100 ml of a 1M solution of citric acid and finally 100 ml of a solution of salt water. The organic phase is dried over sodium sulphate, filtered and concentrated to dryness under vacuum. The oil obtained is washed using isopentane and then crystallized from a dichloromethane/isopentane mixture. A white solid is obtained with a yield of 68%. Melting point: 130-131° C.

1.2) N[2]-[(Benzyloxy)carbonyl]-N[1]-[(3S)-2-Hydroxytetrahydrofuran-3-yl]-L-Leucinamide Under argon, in a three-necked flask containing 60 ml of anhydrous dichloromethane, 1.24 g (3.56 mmol) of intermediate 1.1 is dissolved. The mixture is cooled down to −60° C. before the addition, dropwise, of 10.7 ml (3 eq.) of a 1M solution of DIBAL in dichloromethane. At the end of the addition, the cooling bath is removed and stirring is maintained for another 15 minutes. The reaction medium is then poured carefully into 100 ml of a 20% Rochelle salt solution. After vigorous stirring for 2 hours, 100 ml of dichloromethane is added and the mixture is poured into a separating funnel. The organic phase is recovered and washed with 50 ml of water and 50 ml of salt water. After drying over sodium sulphate and filtration, the organic solution is concentrated to dryness under vacuum. The evaporation residue is purified on a silica column (eluent: ethyl acetate/heptane in proportions of 1/1 to 8/2). A white solid is obtained with a yield of 72%. Melting point: 48-49° C.

1.3) N[2]-[(Benzyloxy)Carbonyl]-N[1]-[(3S)-2-Methoxytetrahydrofuran-3-yl]-L-Leucinamide An excess of trifluoroacetic acid (5 ml) is added, dropwise at 20° C., to a solution of 0.82 g (2.34 mmol) of intermediate 1.2 in 50 ml of methanol. Stirring is maintained for 15 hours at 20° C. The reaction mixture is then partially concentrated under vacuum and taken up in 50 ml of dichloromethane. The organic solution is washed successively with 50 ml of a saturated solution of NaHCO$_3$, 50 ml of water and 50 ml of salt water. After drying over sodium sulphate, filtration and concentration under vacuum, the evaporation residue is purified on a silica column (eluent: ethyl acetate/heptane in proportions of 1/1 to 7/3). A white solid is obtained with a yield of 80%. Melting point: 112-113° C.

1.4) N[1][(3S)-2-Methoxytetrahydrofuran-3-yl]-L-Leucinamide 2 g (5.5 mmol) of intermediate 1.3 and 600 mg of 10% Pd/C are introduced into a stainless steel reactor containing 60 ml of methanol. The mixture is stirred under 2 atm. of hydrogen pressure for 1 hours. After filtration of the catalyst, the methanol is evaporated off under vacuum. The oily residue obtained (1.20 g; 94%) is used as it is in the following stage.

1.5) N-[(Benzyloxy)Carbonyl]-L-Leucyl-N[1]-[(3S)-2-Methoxytetrahydrofuran-3-yl]-L-Leucinamide The experimental protocol used is the same as that described for the synthesis of intermediate 1.1, intermediate 1.4 replacing (S)-2-amino-4-butyrolactone hydrobromide. The reaction product is purified on a silica column (eluent: ethyl acetate/heptane 7/3). 1.04 g of a white solid is obtained with a yield of 69%. Melting point: 76-77° C.

1.6) L-Leucyl-N[1]-[(3S)-2-Methoxytetrahydrofuran-3-yl]-L-Leucinamide

The experimental protocol used is the same as that described for the synthesis of intermediate 1.4, intermediate 1.5 replacing intermediate 1.3. The reaction product is used without additional purification. 0.74 g of a colourless foam is obtained with a yield of 96%.

1.7) N-[(Benzyloxy)Carbonyl]-L-Leucyl-L-Leucyl-N[1]-[(3S)-2-Methoxytetrahydrofuran-3-yl]-L-Leucinamide The experimental protocol used is the same as that described for the synthesis of intermediate 1.1, intermediate 1.6 replacing (S)-2-amino-4-butyrolactone hydrobromide. The reaction product is crystallized from an ethyl acetate/isopentane mixture. 0.96 g of a white solid is obtained with a yield of 77%. Melting point: 210-212° C.

1.8) L-Leucyl-L-Leucyl-N[1]-[(3S)-2-Methoxytetrahydrofuran-3-yl]-L-Leucinamide

The experimental protocol used is the same as that described for the synthesis of intermediate 1.4, intermediate 1.7 replacing intermediate 1.3. 0.74 g of a white solid is obtained with a quantitative yield. Melting point: 187-188° C.

1.9) 1-(10-Acetyl-10H-Phenothiazin-2-yl)Ethanone 30 g (0.118 mol) of 2-acetylphenothiazine and 9.28 g (1 eq.) of acetyl chloride are introduced into a 500 ml flask containing 150 ml of toluene. The reaction mixture is heated to reflux for 45 minutes before the introduction of a new portion of 4.6 g (0,5 eq.) of acetyl chloride. Stirring is maintained under heating at reflux for another 2 hours. The reaction medium is then poured onto approximately 200 g of ice. After stirring, the organic phase is decanted and washed successively with 100 ml of water and 100 ml of salt water. The organic solution is dried over sodium sulphate, filtered and concentrated to dryness using a rotary evaporator. A yellow solid (33 g; 100%) is obtained which is used in the following stage without additional purification.

1.10) 10H-Phenothiazine-2-Carboxylic Acid 24 g (0.084 mol) of intermediate 1.9 is dissolved in 55 ml of pyridine. After the addition of 20.32 g (1 eq.) of iodine, the reaction mixture is heated at 100° C. for 15 minutes. Stirring is then maintained for another 20 hours at 20° C. before concentration to dryness using a rotary evaporator. 100 ml of water is added to the evaporation residue thus obtained, followed by 15 g (4.46 eq.) of NaOH in pellets. This mixture is then heated at 100° C. for 1 hour. After cooling down using an ice bath, the reaction mixture is washed with 100 ml of ethyl acetate. The aqueous solution is then acidified using 50 ml of a 12N aqueous solution of HCl, an abundant precipitate appears. The latter is filtered through a Büchner funnel, washed using ethanol and dried under vacuum at 75° C. An additional portion of the expected product can be recovered from the acid filtrate. The latter is extracted using twice 100 ml of ethyl acetate. The organic phase is then washed with 50 ml of water followed by 50 ml of salt water. After drying over sodium sulphate, the organic solution is concentrated to dryness under vacuum. The total quantity collected is 16.8 g in the form of a yellow solid with a total yield of 82%. Melting point: >235° C.

1.11) N-(10H-Phenothiazin-2-ylcarbonyl)-L-Leucyl-L-Leucyl-N$^1$-[(3S)-2-Methoxytetrahydrofuran-3-yl]-L-Leucinamide The experimental protocol of this peptide condensation is the same as that described for the synthesis of intermediate 1.1, this time using 10H-phenothiazine-2-carboxylic acid (intermediate 1.10) and L-leucyl-L-leucyl-N$^1$-[(3S)-2-methoxytetrahydrofuran-3-yl]-L-leucinamide (intermediate 1.8). The reaction product is purified by chromatography on silica (eluent: ethyl acetate/heptane in proportions of 7/3 to 1/1). 228 mg of a yellow solid is obtained with a yield of 21%. Melting point: 164-165° C.

Example 2

N-(10H-Phenothiazin-2-ylcarbonyl)-L-Leucyl-L-Leucyl-N$^1$-[(3S)-2-Hydroxytetrahydrofuran-3-yl]-L-Leucinamide 228 mg (0,33 mmol) of the compound of Example 1 is dissolved in a flask containing 12 ml of acetone. 2 ml of a 2N aqueous solution of HCl is then added dropwise at 20° C. Stirring is maintained for 6 hours 30 minutes. The reaction medium is then concentrated to dryness and the evaporation residue is purified by chromatography on a silica column (eluent: ethyl acetate/heptane 9/1). 49 mg of a yellow solid is obtained with a yield of 22%. Melting point: 174-176° C.

The compounds of Examples 3 to 6 were prepared according to the same synthesis strategy as that described for the compound of Example 1 starting from intermediates 1.4, 1.6 and 1.10 and appropriate commercial protected amino acids.

Example 3

N-(10H-Phenothiazin-2-ylcarbonyl)Glycyl-N$^1$-[(3S)-2-Methoxytetrahydrofuran-3-yl]-L-Leucinamide Yellow solid.

Example 4

N-(10H-Phenothiazin-2-ylcarbonyl)Leucyl-N$^1$-[(3S)-2-Methoxytetrahydrofuran-3-yl]-L-Leucinamide Yellow solid. Melting point: 180.5° C.

Example 5

N$^6$-[(Benzyloxy)Carbonyl]-N$^2$-(10H-Phenothiazin-2-ylcarbonyl)Lysyl-N$^1$-[(3S)-2-Methoxytetrahydrofuran-3-yl]-L-Leucinamide Yellow solid. Melting point: 102-103° C.

Example 6

1-(10H-Phenothiazin-2-ylcarbonyl)-L-Prolyl-N$^1$-[(3S)-2-Methoxytetrahydrofuran-3-yl]-L-Leucinamide Yellow solid. Melting point: 243-243.5° C.

The compounds of Examples 7, 8, 9 and 10 were prepared according to the experimental protocol described for the compound of Example 2 starting from the compounds of Examples 3, 4, 5 and 6 respectively.

Example 7

N-(10H-Phenothiazin-2-ylcarbonyl)Glycyl-N$^1$-[(3S)-2-Hydroxytetrahydrofuran-3-yl]-L-Leucinamide Yellow solid. Melting point: 126-126.5° C.

Example 8

N-(10H-Phenothiazin-2-ylcarbonyl)Leucyl-N$^1$-[(3S)-2-Hydroxytetrahydrofuran-3-yl]-L-Leucinamide Yellow-green solid. Melting point: 144-144.5° C.

Example 9

N$^6$-[(Benzyloxy)Carbonyl]-N$^2$-(10H-Phenothiazin-2-ylcarbonyl)Lysyl-N$^1$-[(3S)-2-Hydroxytetrahydrofuran-3-yl]-L-Leucinamide Yellow solid. Melting point: 109-109.5° C.

Example 10

1-(10H-Phenothiazin-2-ylcarbonyl)-L-Prolyl-N$^1$-[(3S)-2-Hydroxytetrahydrofuran-3-yl]-L-Leucinamide Pale yellow solid. Melting point: 144.5-145° C.

Example 11

N-(10H-Phenothiazin-2-ylcarbonyl)Leucyl-N$^1$-[(3S)-2-(Acetyloxy)-Tetrahydrofuran-3-yl]-L-Leucinamide 0.62 ml (10 eq.) of acetic anhydride and 40 mg (0.5 eq.) of 4-dimethylaminopyridine are added to a solution of 366 mg (0.66 mmol) of the compound of Example 8 in 6 ml of dichloromethane. The mixture is stirred for 4 hours at 20° C. The solution is then diluted with 20 ml of dichloromethane and 20 ml of a saturated solution of NaHCO$_3$. After stirring and decantation, the organic phase is washed with 20 ml of salt water. The organic solution is then dried over sodium sulphate, filtered and concentrated to dryness under vacuum. The evaporation residue is purified on a silica column (eluent: heptane/AcOEt: 4/6 to 0/1). The pure fractions are collected and concentrated under vacuum. The product is crystallized from a dichloromethane/isopentane mixture. The crystals are filtered, rinsed with isopentane and dried. 180 mg of a pale yellow solid is obtained with a yield of 56%. Melting point: 121-122° C.

Example 12

N$^2$-(10H-Phenothiazin-2-ylcarbonyl)Lysyl-N$^1$-[(3S)-2-Hydroxytetrahydrofuran-3-yl]-L-Leucinamide Trifluoroacetate 0.5 g (0.7 mmole) of the compound of Example 9 is dissolved in 5 ml of acetic acid. After cooling down using an ice bath, 5 ml of an aqueous 33% HBr solution is added dropwise. After stirring for 4 hours at 20° C., the reaction mixture is concentrated to dryness and the evaporation residue is purified by preparative HPLC using a C18 column, 5 μm (eluent: THF/H$_2$O/TFA: 40/60/0.02). After lyophilization, 100 mg of a beige solid is obtained with a yield of 21%.

Example 13

N-(10H-Phenothiazin-2-Ylacetyl)-L-Leucyl-N$^1$-[(3S)-2-Methoxytetrahydrofuran-3-yl]-L-Leucinamide 13.1) 2-(2-Morpholin-4-yl-2-Thioxoethyl)-10H-Phenothiazine The experimental protocol for the preparation of this intermediate is inspired by a synthesis described in the German patent application DE 2 702 714. 24.13 g (0,1 mol) of 2-acetylphenothiazine, 5.13 g (1.6 eq.) of sulphur and 39 ml (4.5 eq.) of morpholine are introduced into a three-necked flask equipped with a thermometer, a condenser and a gas outlet immersing successively into a 2N soda trap and a trap of a concentrated solution of potassium permanganate. The reaction mixture is heated to reflux (internal temperature=119° C.) for 15 hours. After cooling down, this brown solution is poured, under stirring, into 300 ml of absolute ethanol. The mixture is stored for 1 hour at 4° C. in order to initiate crystallization and then overnight at −18° C. The solid obtained is then filtered and rinsed using cold ethanol and heptane. After drying, 27 g of an orange solid is obtained with a yield of 79%.

13.2) 10H-Phenothiazin-2-Ylacetic Acid 31.23 g (91.2 mmol) of intermediate 13.1, 36 g (6 eq.) of 85% potash and 350 ml of absolute ethanol are introduced into a three-necked flask equipped as described previously. The reaction mixture is heated to reflux for 15 hours. After cooling down, this mixture is concentrated to half its volume under vacuum and then poured into 650 ml of water. Under stirring, concentrated sulphuric acid is added to pH 1 and then the mixture is taken to 80° C. After heating for 2 hours, the mixture is cooled down, the precipitate is filtered and rinsed with 4 times 40 ml of water. The solid thus obtained is dissolved in acetone and filtered in order to remove an insoluble solid. The filtrate is then concentrated to dryness under vacuum in order to lead to a pale yellow powder (15.67 g) with a yield of 67%. Melting point: 201.5-202° C.

13.3) N-(10H-Phenothiazin-2-Ylacetyl)-L-Leucyl-N$^1$-[(3S)-2-Methoxytetrahydrofuran-3-yl]-L-Leucinamide The experimental protocol used is the same as that described for Stage 1.11 of Example 1, starting from intermediates 1.6 and 13.2. Beige solid. Melting point: 216-216.5° C.

Example 14

O-(Tert-butyl)-N-(10H-Phenothiazin-2-Ylacetyl)-L-Seryl-N$^1$-[(3S)-2-Methoxytetrahydrofuran-3-yl]-L-Leucinamide 14.1) O-(Tert-butyl)-L-Seryl-N$^1$-[(3S)-2-Methoxytetrahydrofuran-3-yl]-L-Leucinamide This intermediate was prepared in 2 stages according to the experimental protocols described for the synthesis of intermediates 1.5 and 1.6, starting from intermediates 1.4 and commercial Cbz-L-serine(tBu). A colourless oil is obtained.

14.2) O-(Tert-butyl)-N-(10H-Phenothiazin-2-Ylacetyl)-L-Seryl-N$^1$-[(3S)-2-Methoxytetrahydrofuran-3-yl]-L-Leucinamide The experimental protocol used is the same as that described for Stage 1.11 of Example 1, from intermediates 14.1 and 13.2. While solid. Melting point: 179-180° C.

Example 15

N-(10H-Phenothiazin-2-Ylacetyl)-L-Alanyl-3-Cyclohexyl-N$^1$-[(3S)-2-Methoxytetrahydrofuran-3-yl]-L-Alaninamide 15.1) 3-Cyclohexyl-N$^1$-[(3S)-2-Methoxytetrahydrofuran-3-yl]-L-Alaninamide This intermediate was prepared in 4 stages according to the experimental protocols described for Stages 1.1 to 1.4 of Example 1, starting from (S)-2-amino-4-butyrolactone hydrobromide and commercial Cbz-3-cyclohexyl-L-alanine. A colourless oil is obtained.

15.2) L-Alanyl-3-Cyclohexyl-N$^1$-[(3S)-2-Methoxytetrahydrofuran-3-yl]-L-Alaninamide This intermediate was prepared in 2 stages according to the experimental protocols described for the synthesis of intermediates 1.5 and 1.6, starting from intermediate 15.1 and Cbz-L-alanine.

15.3) N-(10H-Phenothiazin-2-Ylacetyl)-L-Alanyl-3-Cyclohexyl-N$^1$-[(3S)-2-Methoxytetrahydrofuran-3-yl]-L-Alaninamide The experimental protocol used is the same as that described for Stage 1.11 of Example 1, starting from intermediates 15.2 and 13.2. A beige solid is obtained. Melting point: 225-226° C.

The compounds of Examples 16, 17 and 18 were prepared according to the experimental protocol described for the compound of Example 2 starting from the compounds of Examples 13, 14 and 15 respectively.

Example 16

N-(10H-Phenothiazin-2-Ylacetyl)-L-Leucyl-N$^1$-[(3S)-2-Hydroxytetrahydrofuran-3-yl]-L-Leucinamide Beige solid. Melting point: 168-168.5° C.

Example 17

O-(Tert-butyl)-N-(10H-Phenothiazin-2-Ylacetyl)-L-Seryl-N$^1$-[(3S)-2-Hydroxytetrahydrofuran-3-yl]-L-Leucinamide Light beige solid. Melting point: 135-136° C.

Example 18

N-(10H-Phenothiazin-2-Ylacetyl)-L-Alanyl-3-Cyclohexyl-N$^1$-[(3S)-2-Hydroxytetrahydrofuran-3-yl]-L-Alaninamide White solid. Melting point: 215-217° C.

Example 19

N-[3-(10H-Phenothiazin-2-yl)Propanoyl]-L-Leucyl-N$^1$-[(3S)-2-Methoxytetrahydrofuran-3-yl]-L-Leucinamide 19.1) 10-Acetyl-10H-Phenothiazine 20 g (0.1 mol) of phenothiazine followed by 14.3 ml (2 eq.) of acetyl chloride are added to a 500 ml flask containing 200 ml of toluene. The heterogeneous reaction mixture is stirred for 1 hour at 50° C. After concentration to dryness, the precipitate is taken up in a minimum of isopentane and filtered. After drying, 24 g of a beige solid is obtained with a quantitative yield. Melting point: 210-211° C.

19.2) 1-(10-Acetyl-10H-Phenothiazin-2-yl)Propan-1-One 150 ml of $CS_2$ is introduced into a multi-necked flask equipped with a mechanical stirrer, an argon supply, a condenser and an addition flask, followed by 24 g of intermediate 19.1. 10.4 ml (1.2 eq.) of propionyl chloride is added, dropwise, to this vigorously-stirred suspension, followed by 50 g (4 eq.) of $AlCl_3$ in one portion, using a solid addition funnel. The funnel is immediately rinsed with an additional 50 ml of $CS_2$. Whilst stirring vigorously, the mixture is heated at 55° C. for 2 hours. The mixture is then cooled down with an ice bath and the $CS_2$ is eliminated using a canula. The hydrolysis of the reaction mixture starts by the gradual addition of small pieces of ice and when the reaction is less virulent the hydrolysis is completed using cold water. The mixture is finally diluted using 300 ml of ethyl acetate and transferred to a separating funnel. The organic solution is decanted, washed twice with 100 ml of water and 100 ml of salt water. After drying over sodium sulphate, filtration and concentration to dryness under vacuum, the residue obtained is triturated in isopentane. This solid is then filtered and rinsed with a minimum amount of isopentane. 13.2 g of a white solid is obtained with a yield of 45%. Melting point: 146.5-147° C.

19.3) 3-(10H-Phenothiazin-2-yl)Propanoic Acid

The experimental protocols used are the same as those described for the syntheses of intermediates 13.1 and 13.2. 2 g of a brown solid is obtained from 6 g of intermediate 19.2, with a total yield (2 stages) of 33%. This compound (80% purity) is used as it is in the following stage.

19.4) N-[3-(10H-Phenothiazin-2-yl)Propanoyl]-L-Leucyl-$N^1$-[(3S)-2-Methoxytetrahydrofuran-3-yl]-L-Leucinamide This example was prepared according to the same synthesis strategy as that described for Stage 1.11 of Example 1 starting from intermediates 1.6 and 19.3. Yellow solid. Melting point: 215-216° C.

Example 20

N-[3-(10H-Phenothiazin-2-yl)Propanoly]-L-Leucyl-$N^1$-[(3S)-2-Hydroxytetrahydrofuran-3-yl]-L-Leucinamide The experimental protocol used is the same as that described for the compound of Example 2, starting with the compound of Example 19. Light beige solid. Melting point: 212-213° C.

Example 21

N-[(10H-Phenothiazin-2-yloxy)Acetyl]-L-Leucyl-$N^1$-[(3S)-2-Methoxytetrahydrofuran-3-yl]-L-Leucinamide 21.1) 10H-Phenothiazin-2-ol A mixture of 25 g (109 mmol) of 2-methoxyphenothiazine and 60 g (4.8 eq.) of pyridinium chloride is heated at 170° C. for 15 hours. After cooling down to a temperature of approximately 80° C., the brown solution obtained is diluted with 200 ml of ethyl acetate. Stirring is maintained for 30 minutes before pouring the reaction mixture into 200 ml of water. After stirring and decantation, the organic phase is dried over sodium sulphate and concentrated to dryness, under vacuum. The greenish solid obtained is recrystallized from 700 ml of boiling toluene. An insoluble solid is eliminated by filtration, the filtrate crystallizes spontaneously overnight. The crystals are collected by filtration and rinsed using isopentane. After drying, 12.43 g of a grey solid is obtained with a yield of 53%. Melting point: 207-208° C.

21.2) Tert-butyl (10H-Phenothiazin-2-yloxy)Acetate

In a 100 ml flask, 1 g (4.6 mmol) of intermediate 21.1 and 1.40 ml (2 eq.) of tert-butyl bromoacetate are dissolved in 25 ml of THF. 1.93 g (3 eq.) of $K_2CO_3$ is added to this solution and the reaction mixture is heated to reflux for 15 hours. After cooling down, 50 ml of water and 50 ml of dichloromethane are added. The organic phase is decanted, washed with 50 ml of water and 50 ml of salt water. After drying over sodium sulphate, filtration and concentration under vacuum, the residue obtained is purified on a silica column, eluent ethyl acetate/heptane (2/8). 940 mg of a cream solid is obtained with a yield of 70%.

21.3) (10H-Phenothiazin-2-yloxy)Acetic Acid 935 mg (2.8 mmol) of intermediate 21.2 is dissolved in 9 ml of dichloromethane. The mixture is cooled down to 0° C. before the addition, dropwise, of 2.19 ml (10 eq.) of trifluoroacetic acid. At the end of the addition, the temperature is allowed to return to 20° C. and stirring is maintained for 3 hours. The reaction mixture is then concentrated to dryness under vacuum and the residue rediluted with 50 ml of ethyl acetate. The organic solution is washed with twice 25 ml of water followed by 25 ml of salt water. After drying over sodium sulphate, filtration and concentration with a rotary evaporator, 540 mg of a pink solid is obtained with a yield of 69%. Melting point: 180-181° C.

21.4) N-[(10H-Phenothiazin-2-yloxy)Acetyl]-L-Leucyl-$N^1$-[(3S)-2-Methoxytetrahydrofuran-3-yl]-L-Leucinamide This example was prepared according to the same synthesis strategy as that described for Stage 1.11 of Example 1 from intermediates 1.6 and 21.3. Beige solid. Melting point: 211.5-212° C.

The compounds of Examples 22 to 35 were prepared according to the same synthesis strategy as that described for the compound of Example 1 starting from intermediates 1.4, 21.3 and the appropriate commercial protected amino acids.

Example 22

N-[(10H-Phenothiazin-2-yloxy)Acetyl]-Glycyl-$N^1$-[(3S)-2-Methoxytetrahydrofuran-3-yl]-L-Leucinamide Beige solid. Melting point: 181-182° C.

Example 23

N-[(10H-Phenothiazin-2-yloxy)Acetyl]-L-Alanyl-$N^1$-[(3S)-Methoxytetrahydrofuran-3-yl]-L-Leucinamide White solid. Melting point: 195-196° C.

Example 24

N-[(10H-Phenothiazin-2-yloxy)Acetyl]-L-Valyl-$N^1$-[(3S)-2-Methoxytetrahydrofuran-3-yl]-L-Leucinamide White solid. Melting point: 240-241° C.

Example 25

N-[(10H-Phenothiazin-2-yloxy)Acetyl]-β-Alanyl-N$^1$-[(3S)-2-Methoxytetrahydrofuran-3-yl]-L-Leucinamide Brown solid. Melting point: 155-157° C.

Example 26

N-Methyl-N-[(10H-Phenothiazin-2-yloxy)Acetyl]Glycyl-N$^1$-[(3S)-2-Methoxytetrahydrofuran-3-yl]-L-Leucinamide Pale pink solid. Melting point: 92-95° C.

Example 27

N-[(10H-Phenothiazin-2-yloxy)Acetyl]-D-Valyl-N$^1$-[(3S)-2-Methoxytetrahydrofuran-3-yl]-L-Leucinamide Light beige solid. Melting point: 204-206° C.

Example 28

3-Methyl-N-[(10H-Phenothiazin-2-yloxy)Acetyl]-L-Valyl-N$^1$-[(3S)-2-Methoxytetrahydrofuran-3-yl]-L-Leucinamide Beige solid. Melting point: 152-153° C.

Example 29

N$^1$-[(3S)-2-Methoxytetrahydrofuran-3-yl]-N$^2$-((2S)-2-{[(10H-Phenothiazin-2-yloxy)-Acetyl]Amino}Butanoyl)-L-Leucinamide Beige solid. Melting point: 164-165° C.

Example 30

N-[(10H-Phenothiazin-2-yloxy)Acetyl]-L-Norvalyl-N$^1$-[(3S)-2-Methoxytetrahydrofuran-3-yl]-L-Leucinamide Beige solid. Melting point: 225-226° C.

Example 31

N-[(10H-Phenothiazin-2-yloxy)Acetyl]-L-Seryl-N$^1$-[(3S)-2-Methoxytetrahydrofuran-3-yl]-L-Leucinamide Grey solid.

Example 32

N-[(10H-Phenothiazin-2-yloxy)Acetyl]-L-Threonyl-N$^1$-[(3S)-2-Methoxytetrahydrofuran-3-yl]-L-Leucinamide Pale yellow solid. Melting point: 92-93° C.

Example 33

N$^1$-[(3S)-2-Methoxytetrahydrofuran-3-yl]-N$^2$-((2S)-2-{[(10H-Phenothiazin-2-yloxy)Acetyl]Amino}-2-Phenylethanoyl)-L-Leucinamide Pale yellow solid. Melting point: 215-217° C.

Example 34

N$^1$-[(3S)-2-Methoxytetrahydrofuran-3-yl]-N$^2$-((2S)-2-{[(10H-Phenothiazin-2-yloxy)Acetyl]Amino}but-3-Enoyl)-L-Leucinamide Pale pink solid.

Example 35

2-Methyl-N-[(10H-Phenothiazin-2-yloxy)Acetyl]Alanyl-N$^1$-[(3S)-2-Methoxytetrahydrofuran-3-yl]-L-Leucinamide Pale pink solid. Melting point: 119-120° C.

Example 36

N-[(10H-Phenothiazin-2-yloxy)Acetyl]-Glycyl-N$^1$-[(3S)-2-Methoxytetrahydrofuran-3-yl]-L-Valinamide 36.1) N$^1$-[(3S)-2-Methoxytetrahydrofuran-3-yl]-L-Valinamide This intermediate was prepared in 4 stages according to the experimental protocols described for Stages 1.1 to 1.4 of Example 1, using (S)-2-amino-4-butyrolactone hydrobromide and Cbz-L-valine. A colourless oil is obtained.

36.2) N-[(10H-Phenothiazin-2-yloxy)Acetyl]-Glycyl-N$^1$-[(3S)-2-Methoxytetrahydrofuran-3-yl]-L-Valinamide This compound was prepared in 3 stages according to the experimental protocols described for Stages 1.5, 1.6 and 1.11 of Example 1 using Cbz-Glycine and intermediates 36.1 and 21.3. A beige solid is obtained.

Example 37

N-[(10H-Phenothiazin-2-yloxy)Acetyl]-Glycyl-3-Cyclohexyl-N$^1$-[(3S)-2-Methoxytetrahydrofuran-3-yl]-L-Alaninamide The synthesis strategy used is the same as that described for Stage 36.2 of Example 36 using Cbz-Glycine and intermediates 15.1 and 21.3. A pale pink solid is obtained. Melting point: 179-180° C.

Example 38

N-[(10H-Phenothiazin-2-yloxy)Acetyl]-Glycyl-N-[(3S)-2-Methoxytetrahydrofuran-3-yl]-L-Phenylalaninamide 38.1) N-[(3S)-2-Methoxytetrahydrofuran-3-yl]-L-Phenylalaninamide This intermediate was prepared in 4 stages according to the experimental protocols described for Stages 1.1 to 1.4 of Example 1, using (S)-2-amino-4-butyrolactone hydrobromide and Cbz-L-phenylalanine. A yellow oil is obtained.

38.2) N-[(10H-Phenothiazin-2-yloxy)Acetyl]-Glycyl-N-[(3S)-2-Methoxytetrahydrofuran-3-yl]-L-Phenylalaninamide The synthesis strategy used is the same as that described for Stage 36.2 of Example 36 using Cbz-Glycine and intermediates 38.1 and 21.3. A beige solid is obtained. Melting point: 203-204° C.

Example 39

N-[(10H-Phenothiazin-2-yloxy)Acetyl]Glycyl-N$^2$-Isobutyl-N$^1$-[(3S)-2-Methoxytetrahydrofuran-3-yl]Glycinamide 39.1) N$^2$-Isobutyl-N$^1$-[(3S)-2-Methoxytetrahydrofuran-3-yl]Glycinamide This intermediate was prepared in 4 stages according to the experimental protocols described for Stages 1.1 to 1.4 of Example 1, using (S)-2-amino-4-butyrolactone hydrobromide and Boc-N-isobutylglycine (J. Med. Chem. (2000), 43(15), 2805-2813). A colourless oil is obtained.

39.2) N-[(10H-Phenothiazin-2-yloxy)Acetyl]Glycyl-N$^2$-Isobutyl-N$^1$-[(3S)-2-Methoxytetrahydrofuran-3-yl]Glycinamide The synthesis strategy used is the same as that described for Stage 36.2 of the example 36, using Cbz-Glycine and intermediates 39.1 and 21.3. A beige solid is obtained. Melting point: 162-164° C.

The compounds of Examples 40 to 58 were prepared according to the experimental protocol described for the compound of Example 2 starting from the compounds of Examples 21 to 39 respectively.

Example 40

N-[(10H-Phenothiazin-2-yloxy)Acetyl]-L-Leucyl-N$^1$-[(3S)-2-Hydroxytetrahydrofuran-3-yl]-L-Leucinamide Light beige solid. Melting point: 141.5-142° C.

Example 41

N-[(10H-Phenothiazin-2-yloxy)Acetyl]-Glycyl-N$^1$-[(3S)-2-Hydroxytetrahydrofuran-3-yl]-L-Leucinamide Pale pink solid. Melting point: 184-186° C.

Example 42

N-[(10H-Phenothiazin-2-yloxy)Acetyl]-L-Alanyl-N$^1$-[(3S)-2-Hydroxytetrahydrofuran-3-yl]-L-Leucinamide Beige solid. Melting point: 144-146° C.

Example 43

N-[(10H-Phenothiazin-2-yloxy)Acetyl]-L-Valyl-N$^1$-[(3S)-2-Hydroxytetrahydrofuran-3-yl]-L-Leucinamide White solid. Melting point: 205-206° C.

Example 44

N-[(10H-Phenothiazin-2-yloxy)Acetyl]-β-Alanyl-N$^1$-[(3S)-2-Hydroxytetrahydrofuran-3-yl]-L-Leucinamide Pale pink solid. Melting point: 161-162° C.

Example 45

N-Methyl-N-[(10H-Phenothiazin-2-yloxy)Acetyl]Glycyl-N$^1$-[(3S)-2-Hydroxytetrahydrofuran-3-yl]-L-Leucinamide Light beige solid. Melting point: 137-138° C.

Example 46

N-[(10H-Phenothiazin-2-yloxy)Acetyl]-D-Valyl-N$^1$-[(3S)-2-Hydroxytetrahydrofuran-3-yl]-L-Leucinamide White solid. Melting point: 145-146° C.

Example 47

3-Methyl-N-[(10H-Phenothiazin-2-yloxy)Acetyl]-L-Valyl-N$^1$-[(3S)-2-Hydroxytetrahydrofuran-3-yl]-L-Leucinamide White solid. Melting point: 157-159° C.

Example 48

N$^1$-[(3S)-2-Hydroxytetrahydrofuran-3-yl]-N$^2$-((2S)-2-{[(10H-Phenothiazin-2-yloxy)Acetyl]Amino}Butanoyl)-L-Leucinamide Beige solid. Melting point: 160-161° C.

Example 49

N-[(10H-Phenothiazin-2-yloxy)Acetyl]-L-Norvalyl-N$^1$-[(3S)-2-Hydroxytetrahydrofuran-3-yl]-L-Leucinamide Beige solid. Melting point: 195-196° C.

Example 50

N-[(10H-Phenothiazin-2-yloxy)Acetyl]-L-Seryl-N$^1$-[(3S)-2-Hydroxytetrahydrofuran-3-yl]-L-Leucinamide Grey solid. Melting point: 128-130° C.

Example 51

N-[(10H-Phenothiazin-2-yloxy)Acetyl]-L-Threonyl-N$^1$-[(3S)-2-Hydroxytetrahydrofuran-3-yl]-L-Leucinamide White solid. Melting point: 195-196° C.

Example 52

N$^1$-[(3S)-2-Hydroxytetrahydrofuran-3-yl]-N$^2$-((2S)-2-{[(10H-Phenothiazin-2-yloxy)Acetyl]Amino}-2-Phenylethanoyl)-L-Leucinamide White solid. Melting point: 137-138° C.

Example 53

N$^1$-[(3S)-2-Hydroxytetrahydrofuran-3-yl]-N$^2$-((2S)-{[(10H-Phenothiazin-2-yloxy)-Acetyl]Amino}but-3-Enoyl)-L-Leucinamide Pale pink solid. Melting point: 159-161° C.

Example 54

2-Methyl-N-[(10H-Phenothiazin-2-yloxy)Acetyl]Alanyl-N$^1$-[(3S)-2-Hydroxytetrahydrofuran-3-yl]-L-Leucinamide Beige solid. Melting point: 138-140° C.

Example 55

N-[(10H-Phenothiazin-2-yloxy)Acetyl]Glycyl-N$^1$-[(3S)-2-Hydroxytetrahydrofuran-3-yl]-L-Valinamide Light beige solid. Melting point: 200-201° C.

Example 56

N-[(10H-Phenothiazin-2-yloxy)Acetyl]Glycyl-3-Cyclohexyl-N$^1$-[(3S)-2-Hydroxytetrahydrofuran-3-yl]-L-Alaninamide Pale pink solid. Melting point: 212-215° C.

Example 57

N-[(10H-Phenothiazin-2-yloxy)Acetyl]Glycyl-N-[(3S)-2-Hydroxytetrahydrofuran-3-yl]-L-Phenylalaninamide Pale yellow solid. Melting point: 207-208° C.

Example 58

N-[(10H-Phenothiazin-2-yloxy)Acetyl]Glycyl-N$^1$-[(3S)-2-Hydroxytetrahydrofuran-3-yl]-N$^2$-Isobutylglycinamide Pink solid. Melting point: 122-124° C.

Example 59

N-[2-Methyl-2-(10H-Phenothiazin-2-yloxy)Propanoyl]Glycyl-N$^1$-[(3S)-2-Methoxytetrahydrofuran-3-yl]-L-Leucinamide 59.1) Tert-butyl 2-Methyl-2-(10H-Phenothiazin-2-yloxy)Propanoate 1.93 g (3 eq.) of K$_2$CO$_3$ is added to a solution of 1 g (4.6 mmol) of intermediate 21.1 in 10 ml of DMF. The reaction mixture was heated to 60° C. before the addition of 1.73 ml (2 eq.) of tert-butyl 2-bromoisobutyrate. The mixture is then taken to 110° C. and stirring is maintained at this temperature for 6 hours. After returning to 20° C., the mixture is poured into 100 ml of water and the product is extracted using twice 100 ml of ethyl acetate. The organic solution is finally washed with 100 ml of salt water, dried over sodium sulphate, filtered and concentrated to dryness under vacuum. The evaporation residue is purified on a silica column, eluent: ethyl acetate/heptane (1/9). 450 mg of a pale pink solid is obtained with a yield of 28%. Melting point: 138-140° C.

59.2) 2-Methyl-2-(10H-Phenothiazin-2-yloxy)Propanoic Acid

The experimental protocol used is the same as that described for intermediate 21.3, intermediate 59.1 replacing intermediate 21.2. 254 mg of a violet solid is obtained with a yield of 67%. Melting point: 177-180° C.

59.3) N-[2-Methyl-2-(10H-Phenothiazin-2-yloxy)Propanoyl]Glycyl-N$^1$-[(3S)-2-Methoxytetrahydrofuran-3-yl]-L-Leucinamide The synthesis strategy used is the same as that described for the synthesis of the compound of Example 22, using glycyl-N$^1$-[(3S)-2-methoxytetrahydrofuran-3-yl]-L-leucinamide (prepared in an analogous manner to intermediate 1.6) and intermediate 59.2. Pale yellow solid. Melting point: 100-104° C.

Example 60

N-[2-Methyl-2-(10H-Phenothiazin-2-yloxy)Propanoyl]Glycyl-N$^1$-[(3S)-2-Hydroxytetrahydrofuran-3-yl]-L-Leucinamide The experimental protocol is the same as that described for the compound of Example 2, starting with the compound of Example 59 instead of the compound of Example 1. A beige solid is obtained. Melting point: 127-128° C.

Example 61

N-(10,11-Dihydro-5H-Dibenzo[b,f]Azepin-3-ylcarbonyl)-L-Leucyl-N$^1$-[(3S)-2-Methoxytetrahydrofuran-3-yl]-L-Leucinamide 61.1) 5-Acetyl-10,11-Dihydro-5H-Dibenzo[b,f]Azepine-3-Carboxylic Acid The experimental protocol used is the same as that described for the synthesis of intermediate 1.10, using 1-(5-acetyl-10,11-dihydro-5H-dibenzo[b,f]azepin-3-yl)ethanone (J. Chem. Soc. 1973, 859-863) as starting product. A pale yellow solid is obtained with a yield of 62%. Melting point: 189-189.5° C.

61.2) 10,11-Dihydro-5H-Dibenzo[b,f]Azepine-3-Carboxylic Acid

A mixture of 3.06 g (10.88 mmol) of intermediate 61.1 and 3 g (45 mmol) of KOH in 35 ml of ethanol is heated to reflux for 15 hours. After cooling down to 0° C., the reaction medium is acidified using 2N HCl to pH=1. The mixture is then extracted using ethyl acetate then the organic solution is washed with water, dried over sodium sulphate, filtered and finally concentrated to dryness. A brown oil is obtained. Mass spectrometry indicates 20% of the expected compound and 70% of acetylated product (intermediate 61.1). The mixture is used as it is in the following stage.

61.3) N-(10,11-Dihydro-5H-Dibenzo[b,f]Azepin-3-ylcarbonyl)-L-Leucyl-N$^1$-[(3S)-2-Methoxytetrahydrofuran-3-yl]-L-Leucinamide This compound was prepared according to the same synthesis strategy as that described for the compound of Example 1, using intermediates 1.6 and 61.2 as starting products.

Example 62

N-(10,11-Dihydro-5H-Dibenzo[b,f]Azepin-3-ylcarbonyl)-L-Leucyl-$N^1$-[(3S)-2-Hydroxytetrahydrofuran-3-yl]-L-Leucinamide The experimental protocol is the same as that described for the compound of Example 2 using the compound of Example 61 as starting product. A light beige solid is obtained. Melting point: 142-143° C.

Example 63

N-[(5-Acetyl-10,11-Dihydro-5H-Dibenzo[b,f] Azepin-3-yl)Carbonyl]-L-Leucyl-$N^1$-[(3S)-2-Methoxytetrahydrofuran-3-yl]-L-Leucinamide This compound was prepared according to the same synthesis strategy as that described for the compound of Example 1, using intermediates 1.6 and 61.1 as starting products.

Example 64

2-Methyl-N-[(10H-Phenothiazin-2-yloxy)Acetyl] Alanyl-$N^1$-[(3S)-2-Hydroxytetrahydrofuran-3-yl]-L-Leucinamide The experimental protocol is the same as that described for Example 2, the compound of Example 63 replacing the compound of Example 1. A white solid is obtained. Melting point: 166-167° C.

Pharmacological Study of the Compounds of the Invention

Study of Effects on Human Calpain I

The test consists of measuring the activity of the enzyme (purified enzyme from human erythrocytes) which is incubated in a buffer in the presence of a peptide substrate coupled to a fluorochrome (amino-methylcoumarin, AMC) and calcium. The enzyme activated by the calcium proteolyzes the substrate and releases the AMC fragment. The released AMC fluoresces at 460 nm under excitation at 380 nm. The activity of the enzyme is therefore proportional to the quantity of fluorescence, i.e. free AMC fragment. The fluorescence (380/460 nm) is measured using a multi-well fluorometer (Victor 2, Wallac).

The assay is carried out in 96-well micro-plates with a transparent base and black walls in which 10 µl per well of substance to be tested are distributed, in 10% DMSO, 45 µl of reaction mixture containing human calpain 1 at 2.2 U/ml (Calbiochem, ref: 208713), Suc Leu Tyr-AMC substrate (Bachem, ref: 1-1355) at 1.1 mM in buffer (110 mM Tris-HCl; 110 mM NaCl; 2.2 mM EDTA; 2.2 mM EGTA; 1.1 mM mercaptoethanol). The reaction is initiated by adding 45 µl of 22 mM $CaCl_2$. In order to determine the background noise, control wells without calcium are added to the plate (10 µL 10% DMSO +45 µl of buffer with the enzyme and the substrate +45 µl $H_2O$). In order to determine the total activity of the enzyme, control wells without product are added to the plate (10 µL 10% DMSO +45 µl of buffer with the enzyme and the substrate +45 µl of 22 mM $CaCl_2$). Each concentration of the products (0.1 nM to 10 µM) is tested in duplicate. The plates are shaken and incubation takes place in darkness for one hour at 25° C. The fluorescence is read at 380-460 nm using the fluorometer.

The compounds of Examples 2, 7 to 12, 16 to 18, 20, 40 to 53, 55 to 57, 60, 62 and 64 have an $IC_{50}$ less than or equal to 5 µM in this test.

Study of the in situ Effects on Calpain Activity in Rat (C6) Glial Cells

Rat C6 glial cells are seeded at 25,000 cells per well in 96-well plates in DMEM 10% FBS. The next day, the cells which have adhered are washed 3 times in DMEM medium without serum and 40 mM Hepes. One hundred microliters of the calpain inhibitor are deposited in the wells. After incubation for one hour at 37° C. under a 5% $CO_2$ atmosphere, 10 µl containing the fluorescent calpain substrate (Suc-Leu-Tyr-AMC) and maitotoxin (Sigma, ref: M-9159), in order to obtain a final concentration in the well of 100 µM and 1 nM respectively, are added.

In order to determine the total activity of the cell enzyme, wells without product are added to the plate (100 µl DMSO $100^{th}$ plus 10 µl of MTX and substrate). The background noise is determined by adding control wells without MTX. Each concentration of inhibitor (0.01 µM to 100 µM) is tested in triplicate. The plates are shaken, the fluorescence is read at 380/460 nm using Victor at T zero. Incubation took place for one hour thirty minutes for the C6 cells at 30° C. in darkness. The compounds of Examples 8, 9, 11, 16, 20, 40, 43 and 47 to 53 have an $IC_{50}$ less than or equal to 10 µM in this test.

Study of the Effects on Lipid Peroxidation of Rat Cerebral Cortex

The inhibitory activity of the products of the invention is determined by measuring their effects on the degree of lipid peroxidation, determined by the malondialdehyde (MDA) concentration. The MDA produced by the peroxidation of the unsaturated fatty acids is a good indication of lipid peroxidation (H Esterbauer and K H Cheeseman, *Meth. Enzymol.* (1990), 186, 407-421). Male Sprague Dawley rats weighing 200 to 250 g (Charles River) were sacrificed by decapitation. The cerebral cortex is removed, then homogenized using a Thomas potter in 20 mM Tris-HCl buffer, pH=7.4. The homogenate is centrifuged twice at 50,000 g for 10 minutes at 4° C. The pellet is kept at −80° C. On the day of the experiment, the pellet is replaced in suspension at a concentration of 1 g/15 ml and centrifuged at 515 g for 10 minutes at 4° C. The supernatant is used immediately to determine the lipid peroxidation. The rat cerebral cortex homogenate (500 µl) is incubated at 37° C. for 15 minutes in the presence of the compounds to be tested or solvent (10 µl). The lipid peroxidation reaction is initiated by the addition of 50 µl of 1 mM $FeCl_2$, 1 mM EDTA and 4 mM ascorbic acid. After incubation for 30 minutes at 37° C., the reaction is stopped by the addition of 50 µl of a solution of di-tert-butyl hydroxyl toluene (BHT, 0.2%). The MDA is quantified using a colorimetric test, by reacting a chromogenic reagent (R), N-methyl-2-phenylindole (650 µl) with 200 µl of the homogenate for 1 hour at 45° C. The condensation of an MDA molecule of with two molecules of reagent R produces a stable chromophore the maximum absorbance wavelength of which is equal to 586 nm. (Caldwell et al., *European J. Pharmacol.* (1995), 285, 203-206).

The compounds of Examples 2, 7 to 9, 11, 12, 16, 17, 20, 40 to 45, 56, 57, 60 and 62 have an $IC_{50}$ less than or equal to 5 µM in this test.

The invention claimed is:
1. A compound of the formula

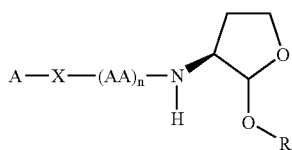

wherein A is

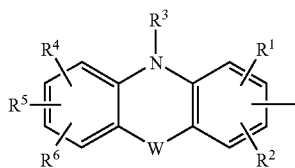

$R^1$, $R^2$, $R^4$, $R^5$ and $R^6$ are independently selected from the group consisting of hydrogen, halogen, OH, alkyl, alkoxy, cyano, nitro and $NR^7R^8$, $R^7$ and $R^8$ are independently selected from the group consisting of hydrogen, alkyl and —$COR^9$, $R^9$ is selected from the group consisting of hydrogen, alkyl and alkoxy, $R^3$ is selected from the group consisting of hydrogen, alkyl and —$COR^{10}$, $R^{10}$ is selected from the group consisting of hydrogen, alkyl and alkoxy, and W is selected from the group consisting of a bond, —$CH_2$—$CH_2$—, —CH=CH—, —O—, —S— and —$NR^{11}$— in which $R^{11}$ is hydrogen or alkyl;

X is selected from the group consisting of —CO—, —Y—CO—, —O—Y—CO— and —$NR^{12}$—Y—CO—, Y is alkylene or haloalkylene, $R^{12}$ is hydrogen, alkyl and —$COR^{13}$, $R^{13}$ is selected from the group consisting of hydrogen, alkyl, haloalkyl and alkoxy, AA is, each time that it occurs, selected from the group consisting of a natural amino acid, a natural amino acid the side chain of which is protected by a member selected from the group consisting of:

alkyl or aralkyl ester when it bears a carboxylic acid function, alkyl carbamate, aralkyl carbamate, alkyl carboxamide and aralkyl carboxamide when it bears an amine function, alkyl ether, aralkyl ether, alkyl ester and aralkyl ester when it bears an alcohol function, alkyl or aralkyl thioether when it bears a thiol function and an amino acid of the formula $NR^{14}$—$(CH_2)_p$—$CR^{15}R^{16}$—CO— in which p is 0 or 1, $R^{14}$ is hydrogen or alkyl, $R^{15}$ is hydrogen or alkyl, $R^{16}$ is selected from the group consisting of hydrogen, alkyl, haloalkyl, phenyl, cycloalkyl, cycloalkylalkyl and alkenyl, n is 2 or 3; and finally or —$(AA)_2$— is —$NR^{17}$—$(CH_2)_3$—$CH(R^{18})$—CO— in which $R^{17}$ is hydrogen or alkyl and $R^{18}$ is hydrogen or alkyl;

R is selected from the group consisting of hydrogen, alkyl and —CO—$R^{19}$ $R^{19}$ is alkyl;

or a salt thereof.

2. A compound of claim 1, wherein:

$R^1$, $R^2$, $R^4$, $R^5$ and $R^6$ are independently selected from the group consisting of hydrogen, halogen alkyl, alkoxy an alkyl, alkoxy and —$NR^7R^8$;

$R^3$ is selected from the group consisting of hydrogen, methyl and —$COR^9$ in which $R^9$ is methyl or tert-butoxy;

W is selected from the group consisting of a bond —$CH_2$—$CH_2$—, —CH=CH—, O and —S—;

X is selected from the group consisting of —CO—, —Y—CO— and —O—Y—CO—;

—$(AA)_n$— contains amino acids chosen independently from the group consisting of natural amino acids, 3-methylvaline, norvaline, phenylglycine, vinylglycine and 2-aminobutyric acid;

n is 2; and

R is hydrogen or methyl;

or a salt thereof.

3. A compound of claim 1, wherein $R^1$, $R^2$, $R^4$, $R^5$ and $R^6$ are independently selected from the group consisting of hydrogen alkyl and alkoxy;

$R^3$ is hydrogen or methyl;

W is —O— or —S—;

X is —Y—CO— or —O—Y—CO—;

—$(AA)_n$— is an —$(AA^2)$—$(AA^1)$— such that $AA^1$ is Leu and $AA^2$ is an amino acid chosen from the group consisting of natural amino acids, 3-methylvaline, norvaline, phenylglycine, vinylglycine and 2-aminobutyric acid;

R is hydrogen, or a salt thereof.

4. A compound of claim 1 is selected from the group consisting of:

N-(10H-phenothiazin-2-ylcarbonyl)-L-leucyl-L-leucyl-$N^1$-[(3S)-2-methoxytetrahydrofuran-3-yl]-L-leucinamide;

N-(10H-phenothiazin-2-ylcarbonyl)-L-leucyl-L-leucyl-$N^1$-[(3S)-2-hydroxytetrahydrofuran-3-yl]-L-leucinamide;

N-(10H-phenothiazin-2-ylcarbonyl)glycyl-$N^1$-[(3S)-2-methoxytetrahydrofuran-3-yl]-L-leucinamide;

N-(10H-phenothiazin-2-ylcarbonyl)leucyl-$N^1$-[(3S)-2-methoxytetrahydrofuran-3-yl]-L-leucinamide;

$N^6$-[(3S)-2-methoxytetrahydrofuran-3-yl]-L-leucinamide;

1-(10H-phenothiazin-2-ylcarbonyl)-L-prolyl-$N^1$-[(3S)-2-methoxytetrahydrofuran-3-yl]-L-leucinamide;

N-(10H-phenothiazin-2-ylcarbonyl)glycyl-$N^1$-[(3S)-2-hydroxytetrahydrofuran-3-yl]-L-leucinamide;

N-(10H-phenothiazin-2-ylcarbonyl)leucyl-$N^1$-[(3S)-2-hydroxytetrahydrofuran-3-yl]-L-leucinamide;

N-[(10H-phenothiazin-2-yloxy)acetyl]-L-alanyl-$N^1$-[(3S)-2-methoxytetrahydrofuran-3-yl]-L-leucinamide;

N-[(10H-phenothiazin-2-yloxy)acetyl]-L-valyl-$N^1$[(3S)-2-methoxytetrahydrofuran-3-yl]-L-leucinamide;

N-[(10H-phenothiazin-2-yloxy)acetyl]-β-alanyl-$N^1$-[(3S)-2-methoxytetrahydrofuran-3-yl]-L-leucinamide;

N-methyl-N-[(10H-phenothiazin-2-yloxy)acetyl]glycyl-$N^1$-[(3S)-2-methoxytetrahydrofuran-3-yl]-L-leucinamide;

N-[(10H-phenothiazin-2-yloxy)acetyl]-D-valyl-$N^1$-[(3S)-2-methoxytetrahydrofuran-3-yl]-L-leucinamide;

3-methyl-N-[(10H-phenothiazin-2-yloxy)acetyl]-L-valyl-N$^1$-[(3S)-2-methoxytetrahydrofuran-3-yl]-L-leucinamide;

N$^1$-[(3S)-2-methoxytetrahydrofuran-3-yl]-N$^2$-((2S)-2-{[(10H-phenothiazin-2-yloxy)-acetyl]amino}butanoyl)-L-leucinamide;

N-[(10H-phenothiazin-2-yloxy)acetyl]-L-norvalyl-N$^1$-[(3S)-2-methoxytetrahydrofuran-3-yl]-L-leucinamide;

N-[(10H-phenothiazin-2-yloxy)acetyl]-L-seryl-N$^1$-[(3S)-2-methoxytetrahydrofuran-3-yl]-L-leucinamide;

N-[(10H-phenothiazin-2-yloxy)acetyl]-L-threonyl-N$^1$-[(3S)-2-methoxytetrahydrofuran-3-yl]-L-leucinamide;

N$^1$-[(3S)-2-methoxytetrahydrofuran-3-yl]-N$^2$-((2S)-2{[(10H-phenothiazin-2-yloxy)acetyl]amino}-2-phenylethanoyl)-L-leucinamide;

N$^1$-[(3S)-2-methoxytetrahydrofuran-3-yl]-N$^2$-((2S)-2-{[(10H-phenothiazin-2-yloxy)acetyl]amino}but-3-enoyl)-L-leucinamide;

2-methyl-N-[(10H-phenothiazin-2-yloxy)acetyl]alanyl-N$^1$-[(3S)-2-methoxytetrahydrofuran-3-yl]-L-leucinamide;

N$^6$-[(benzyloxy)carbonyl]-N$^2$-(10H-phenothiazin-2-ylcarbonyl)lysyl-N$^1$-[(3S)-2-hydroxytetrahydrofuran-3-yl]-L-leucinamide;

1-(10H-phenothiazin-2-ylcarbonyl)-L-prolyl-N$^1$-[(3S)-2-hydroxytetrahydrofuran-3-yl]-L-leucinamide;

N-(10H-phenothiazin-2-ylcarbonyl)leucyl-N$^1$-[(3S)-2-(acetyloxy)-tetrahydrofuran-3-yl]-L-leucinamide;

N$^2$-(10H-phenothiazin-2-ylcarbonyl)lysyl-N$^1$-[(3S)-2-hydroxytetrahydrofuran-3-yl]-L-leucinamide;

N-(10H-phenothiazin-2-ylacetyl)-L-leucyl-N$^1$-[(3S)-2-methoxytetrahydrofuran-3-yl]-L-leucinamide;

O-(tert-butyl)-N-(10H-phenothiazin-2-ylacetyl)-L-seryl-N$^1$-[(3S)-2-methoxytetrahydrofuran-3-yl]-L-leucinamide;

N-(10H-phenothiazin-2-ylacetyl)-L-alanyl-3-cyclohexyl-N$^1$-[(3S)-2-methoxytetrahydrofuran-3-yl]-L-alaninamide;

N-(10H-phenothiazin-2-ylacetyl)-L-leucyl-N$^1$-[(3S)-2-hydroxytetrahydrofuran-3-yl]-L-leucinamide;

O-(tert-butyl)-N-(10H-phenothiazin-2-ylacetyl)-L-seryl-N$^1$-[(3S)-2-hydroxytetrahydrofuran-3-yl]-L-leucinamide;

N-(10H-phenothiazin-2-ylacetyl)-L-alanyl-3-cyclohexyl-N$^1$-[(3S)-2-hydroxytetrahydrofuran-3-yl]-L-alaninamide;

N-[3-(10H-phenothiazin-2-yl)propanoyl]-L-leucyl-N$^1$-[(3S)-2-methoxytetrahydrofuran-3-yl]-L-leucinamide;

N-[3-(10H-phenothiazin-2-yl)propanoyl]-L-leucyl-N$^1$-[(3S)-2-hydroxytetrahydrofuran-3-yl]-L-leucinamide;

N-[(10H-phenothiazin-2-yloxy)acetyl]-L-leucyl-N$^1$-[(3S)-2-methoxytetrahydrofuran-3-yl]-L-leucinamide;

N-[(10H-phenothiazin-2-yloxy)acetyl]-glycyl-N$^1$-[(3S)-2-methoxytetrahydrofuran-3-yl]-L-leucinamide;

N-[(10H-phenothiazin-2-yloxy)acetyl]-glycyl-N$^1$-[(3S)-2-methoxytetrahydrofuran-3-yl]-L-valinamide;

N-[(10H-phenothiazin-2-yloxy)acetyl]-glycyl-3-cyclohexyl-N$^1$-[(3S)-2-methoxytetrahydrofuran-3-yl]-L-alaninamide;

N-[(10H-phenothiazin-2-yloxy)acetyl]-glycyl-N-[(3S)-2-methoxytetrahydrofuran-3-yl]-L-phenylalaninamide;

N-[(10H-phenothiazin-2-yloxy)acetyl]glycyl-N$^2$-isobutyl-N$^1$-[(3S)-2-methoxytetrahydrofuran-3-yl]glycinamide;

N-[(10H-phenothiazin-2-yloxy)acetyl]-L-leucyl-N$^1$-[(3S)-2-hydroxytetrahydrofuran-3-yl]-L-leucinamide;

N-[(10H-phenothiazin-2-yloxy)acetyl]-glycyl-N$^1$-[(3S)-2-hydroxytetrahydrofuran-3-yl]-L-leucinamide;

N-[(10H-phenothiazin-2-yloxy)acetyl]-L-alanyl-N$^1$-[(3S)-2-hydroxytetrahydrofuran-3-yl]-L-leucinamide;

N-[(10H-phenothiazin-2-yloxy)acetyl]-L-valyl-N$^1$-[(3S)-2-hydroxytetrahydrofuran-3-yl]-L-leucinamide;

N-[(10H-phenothiazin-2-yloxy)acetyl]-β-alanyl-N$^1$-[(3S)-2-hydroxytetrahydrofuran-3-yl]-L-leucinamide;

N-methyl-N-[(10H-phenothiazin-2-yloxy)acetyl]glycyl-N$^1$-[(3S)-2-hydroxytetrahdyrofuran-3-yl]-L-leucinamide;

N-[(10H-phenothiazin-2-yloxy)acetyl]-D-valyl-N$^1$-[(3S)-2-hydroxytetrahydrofuran-3-yl]-L-leucinamide;

3-methyl-N-[(10H-phenothiazin-2-yloxy)acetyl]-L-valyl-N$^1$-[(3S)-2-hydroxytetrahydrofuran-3-yl]-L-leucinamide;

N$^1$-[(3S)-2-hydroxytetrahydrofuran-3-yl]-N$^2$-((2S)-2-{[(10H-phenothiazin-2-yloxy)acetyl]amino}butanoyl)-L-leucinamide;

N-[(10H-phenothiazin-2-yloxy)acetyl]-L-norvalyl-N$^1$-[(3S)-2-hydroxytetrahydrofuran-3-yl]-L-leucinamide;

N-[(10H-phenothiazin-2-yloxy)acetyl]-L-seryl-N$^1$-[(3S)-2-hydroxytetrahydrofuran-3-yl]-L-leucinamide;

N-[(10H-phenothiazin-2-yloxy)acetyl]-L-threonyl-N$^1$-[(3S)-2-hydroxytetrahydrofuran-3-yl]-L-leucinamide;

N$^1$-[(3S)-2-hydroxytetrahydrofuran-3-yl]-N$^2$-((2S)-2-{[(10H-phenothiazin-2-yloxy)acetyl]amino}-2-phenylethanoyl)-L-leucinamide;

N$^1$-[(3S)-2-hydroxytetrahydrofuran-3-yl]-N$^2$-((2S)-2-{[(10H-phenothiazin-2-yloxy)-acetyl]amino}but-3-enoyl)-L-leucinamide;

2-methyl-N-[(10H-phenothiazin-2-yloxy)acetyl]alanyl-N$^1$-[(3S)-2-hydroxytetrahydrofuran-3-yl]-L-leucinamide;

N-[(10H-phenothiazin-2-yloxy)acetyl]glycyl-N$^1$-[(3S)-2-hydroxytetrahydrofuran-3-yl]-L-valinamide;

N-[(10H-phenothiazin-2-yloxy)acetyl]glycyl-3-cyclohexyl-N$^1$-[(3S)-2-hydroxytetrahydrofuran-3-yl]-L-alaninamide;

N-[(10H-phenothiazin-2-yloxy)acetyl]glycyl-N-[(3S)-2-hydroxytetrahydrofuran-3-yl]-L-phenylalaninamide;

N-[(10H-phenothiazin-2-yloxy)acetyl]glycyl-N$^1$-[(3S)-2-hydroxytetrahydrofuran-3-yl]-N$^2$-isobutylglycinamide;

N-[(2-methyl-2-(10H-phenothiazin-2-yloxy)propanoyl]glycyl-N$^1$-[(3S)-2-methoxytetrahydrofuran-3-yl]-L-leucinamide;

N-[2-methyl-2-(10H-phenothiazin-2-yloxy)propanoyl]glycyl-N$^1$-[(3S)-2-hydroxytetrahydrofuran-3-yl]-L-leucinamide;

N-(10,11-dihydro-5H-dibenzo[b,f]azepin-3-ylcarbonyl)-L-leucyl-N$^1$-[(3S)-2-methoxytetrahydrofuran-3-yl]-L-leucinamide;

N-(10,11-dihydro-5H-dibenzo[b,f]azepin-3-ylcarbonyl)-L-leucyl-N$^1$-[(3S)-2-hydroxytetrahydrofuran-3-yl]-L-leucinamide;

N-[(5-acetyl-10,11-dihydro-5H-dibenzo[b,f]azepin-3-yl)carbonyl]-L-leucyl-N$^1$-[(3S)-2-methoxytetrahydrofuran-3-yl]-L-leucinamide;

2-methyl-N-[(10H-phenothiazin-2-yloxy)acetyl]alanyl-N$^1$-[(3S)-2-hydroxytetrahydrofuran-3-yl]-L-leucinamide; and or a salt thereof.

* * * * *